US008610071B2

(12) United States Patent
Kamba et al.

(10) Patent No.: US 8,610,071 B2
(45) Date of Patent: Dec. 17, 2013

(54) METHOD OF MEASURING CHARACTERISTICS OF SPECIMEN, AND FLAT-PLATE PERIODIC STRUCTURE

(71) Applicant: Murata Manufacturing Co., Ltd., Nagaokakyo (JP)

(72) Inventors: Seiji Kamba, Nagaokakyo (JP); Kazuhiro Takigawa, Nagaokakyo (JP); Takashi Kondo, Nagaokakyo (JP); Koji Tanaka, Nagaokakyo (JP)

(73) Assignee: Murata Manufacturing Co., Ltd., Nagaokakyo-Shi, Kyoto-fu (JP)

(*) Notice: Subject to any disclaimer, the term of this patent is extended or adjusted under 35 U.S.C. 154(b) by 0 days.

(21) Appl. No.: 13/780,108

(22) Filed: Feb. 28, 2013

(65) Prior Publication Data
US 2013/0221209 A1 Aug. 29, 2013

Related U.S. Application Data

(63) Continuation of application No. PCT/JP2011/069186, filed on Aug. 25, 2011.

(30) Foreign Application Priority Data

Sep. 1, 2010 (JP) .................................. 2010-195486

(51) Int. Cl.
*G01N 21/35* (2006.01)
*G01J 3/02* (2006.01)
(52) U.S. Cl.
USPC ............... 250/339.07; 250/336.1; 250/339.06
(58) Field of Classification Search
USPC .................. 250/336.1, 338.1, 339.06–339.08
See application file for complete search history.

(56) References Cited

U.S. PATENT DOCUMENTS

| 8,253,103 B2 | 8/2012 | Ogawa et al. |
| 2010/0025586 A1* | 2/2010 | Ogawa et al. ............... 250/341.1 |
| 2012/0008142 A1* | 1/2012 | Kamba et al. ................ 356/328 |

FOREIGN PATENT DOCUMENTS

| JP | 2008-185552 A | 8/2008 |
| JP | 2010117690 A | 5/2010 |

OTHER PUBLICATIONS

International Search Report and Written Opinion, issued in PCT/JP2011/069186, mailed Nov. 29, 2011.
Masanori Hagiyuki, et al., "Development and applications of metamaterials in terahertz region," Oyo Butsuri, Jun. 10, 2009, vol. 78, No. 6, pp. 511-517.

* cited by examiner

*Primary Examiner* — Casey Bryant
(74) *Attorney, Agent, or Firm* — Dickstein Shapiro LLP

(57) ABSTRACT

The present invention provides a measuring method comprising the steps of holding a specimen on a flat-plate periodic structure, applying a linearly-polarized electromagnetic wave to the periodic structure, and measuring characteristics of the specimen based on change of the electromagnetic wave scattered forward or backward by the periodic structure, wherein the periodic structure is structured such that plural unit structures having the same shape are two-dimensionally and periodically interconnected in a direction of one reference plane, the unit structure has at least one aperture penetrating therethrough in a direction perpendicular to the reference plane, the electromagnetic wave is applied from a direction perpendicular to the reference plane, and the unit structure has a shape that is not mirror-symmetric with respect to an imaginary plane orthogonal to a polarizing direction of the electromagnetic wave.

12 Claims, 33 Drawing Sheets

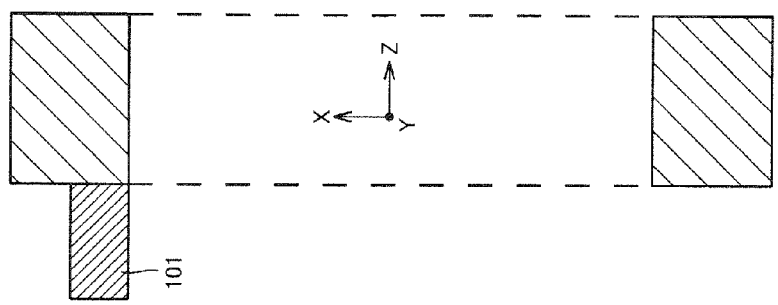
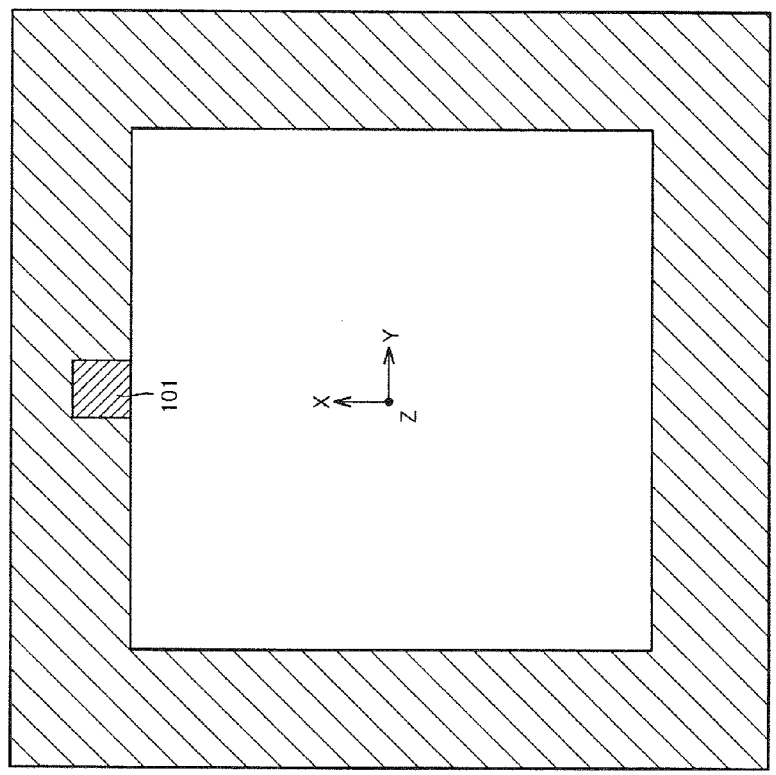

YZ OBSERVATION PLANE

XY OBSERVATION PLANE

XZ OBSERVATION PLANE

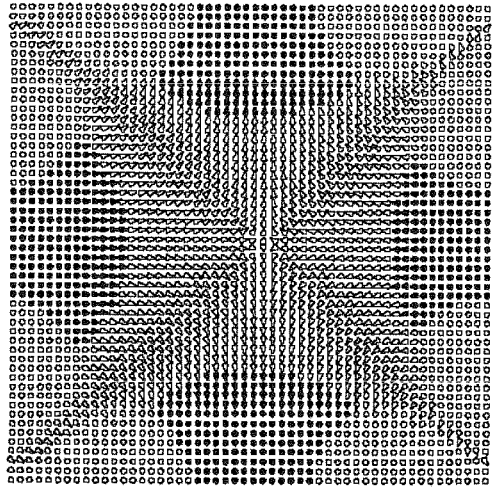
FIG. 10C
YZ OBSERVATION PLANE
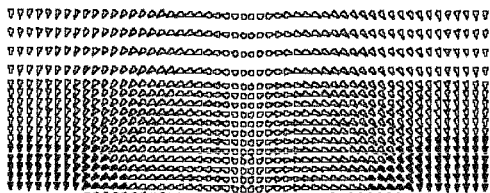
FIG. 10B
XY OBSERVATION PLANE
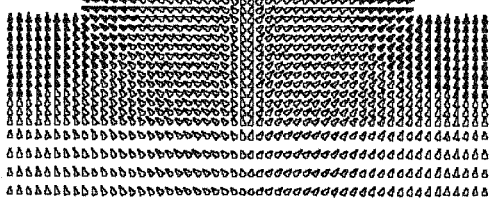
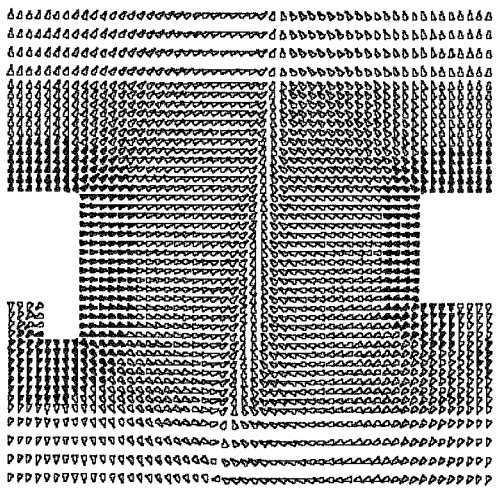
FIG. 10A
XZ OBSERVATION PLANE

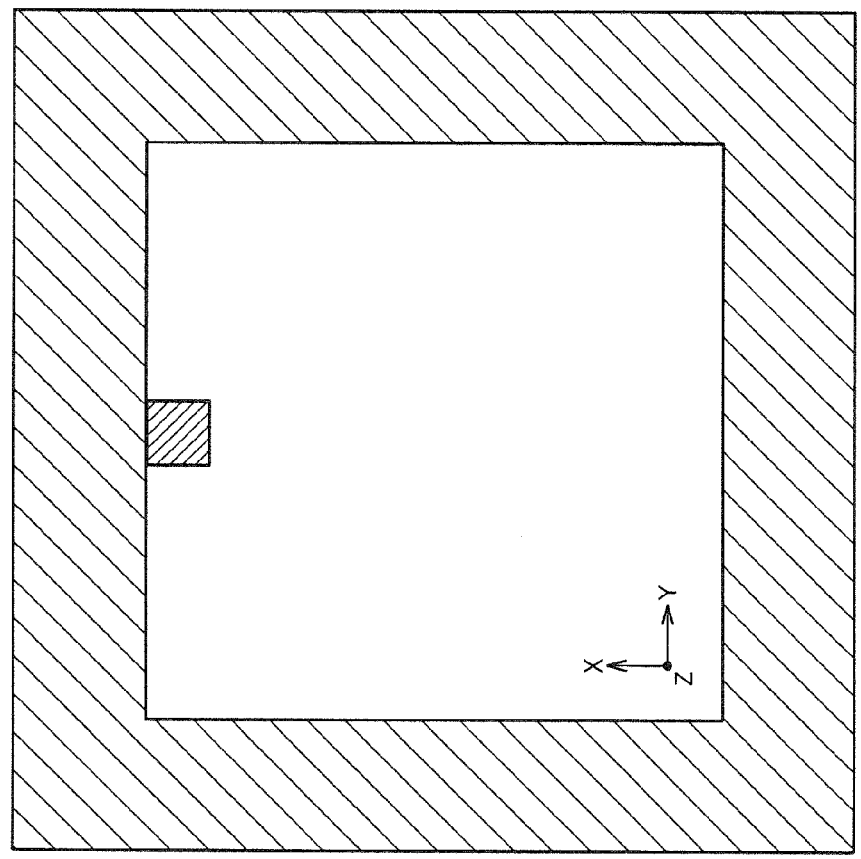

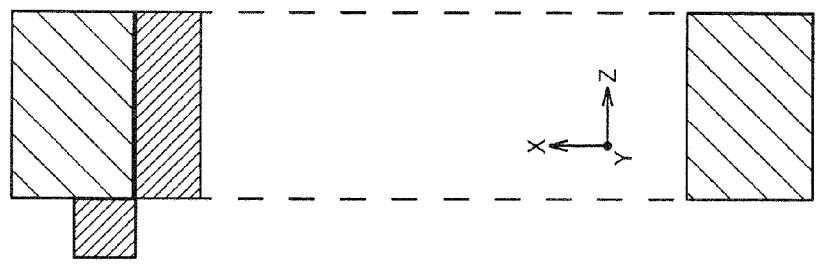
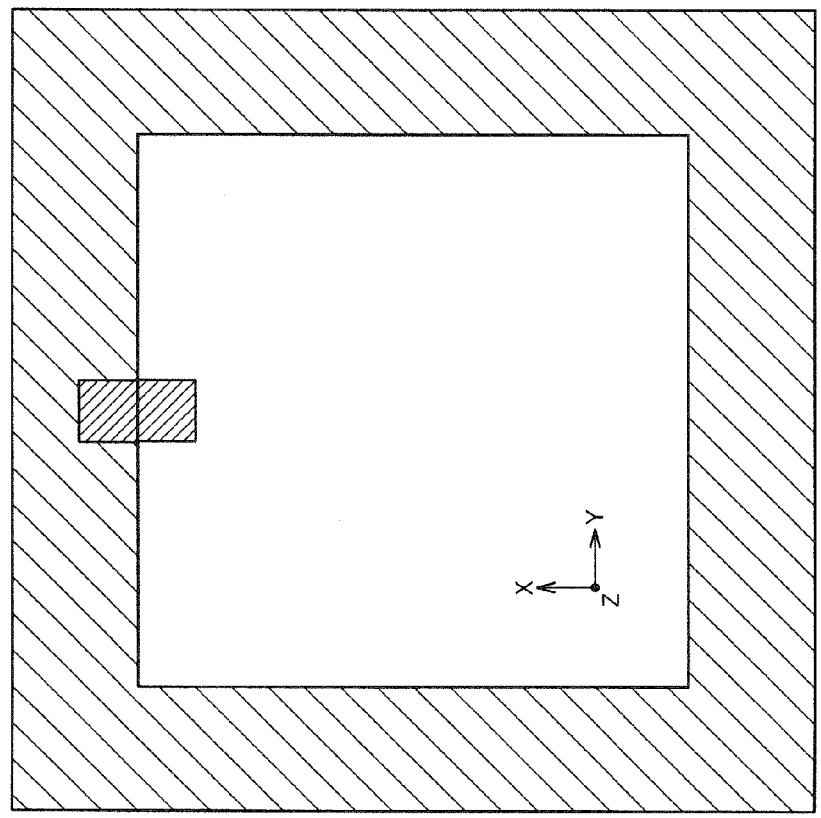
FIG. 22B
FIG. 22A

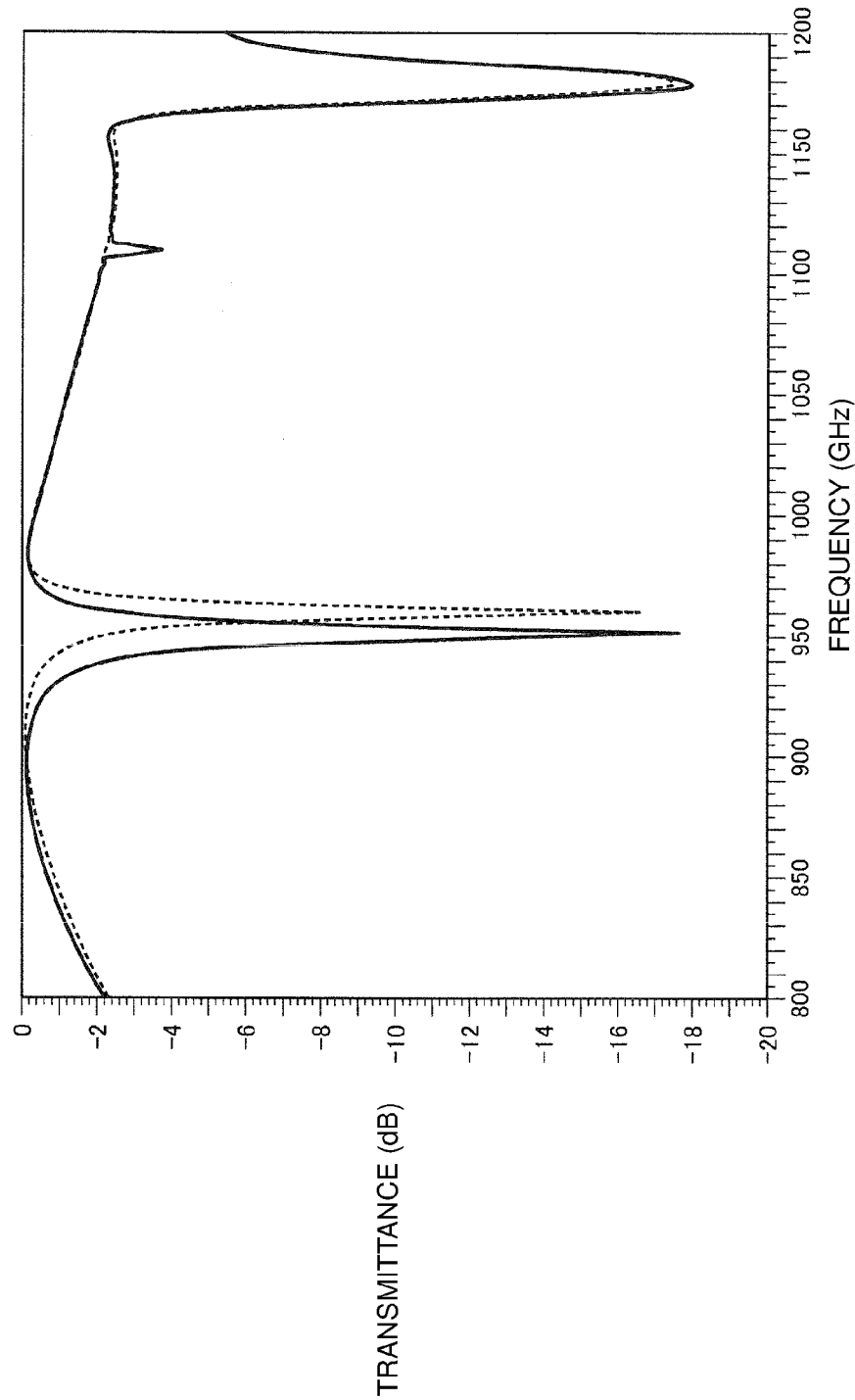

TE10 MODE

METHOD OF MEASURING CHARACTERISTICS OF SPECIMEN, AND FLAT-PLATE PERIODIC STRUCTURE

This is a continuation of application Serial No. PCT/JP2011/069186, filed Aug. 25, 2011, the entire contents of which are incorporated herein by reference.

TECHNICAL FIELD

The present invention relates to a method of, with intent to analyze characteristics of a substance, holding a specimen on a flat-plate periodic structure, applying an electromagnetic wave to the flat-plate periodic structure on which the specimen is held, detecting the electromagnetic wave scattered by the specimen, and measuring characteristics of the specimen. The present invention also relates to the flat-plate periodic structure that is used to carry out the measuring method.

BACKGROUND ART

To analyze characteristics of a substance, a measurement method has hitherto been used which includes the steps of holding a specimen on an aperture array structure (i.e., a flat-plate periodic structure that is made up of plural unit structures each having an aperture), applying an electromagnetic wave to the aperture array structure on which the specimen is held, and analyzing a transmission spectrum of the electromagnetic wave, thereby detecting characteristics of the specimen. One practical example is a method of applying a terahertz wave to a specimen, such as a protein attached to a metal mesh filter, for example, and analyzing a transmission spectrum of the terahertz wave.

As an example of that type of related-art method of analyzing a transmission spectrum using an electromagnetic wave, Patent Document 1 (Japanese Unexamined Patent Application Publication No. 2008-185552) discloses a measurement method of applying an electromagnetic wave to an aperture array structure having an aperture region (specifically, a mesh-like conductive plate), on which a specimen is held, from a direction oblique to a direction perpendicular to a principal surface of the aperture array structure, measuring the electromagnetic wave having transmitted through the aperture array structure, and detecting characteristics of the specimen based on a phenomenon that a position of a dip waveform, which appears in the frequency characteristic of a measured value, is shifted depending on the presence of the specimen.

CITATION LIST

Patent Document

Patent Document 1: Japanese Unexamined Patent Application Publication No. 2008-185552

SUMMARY OF INVENTION

Technical Problem

In the measurement method of this prior art in which the electromagnetic wave applied to the aperture array structure (i.e., the flat-plate periodic structure) is obliquely incident upon the principal surface of the aperture array structure, there has been a problem that because the dip waveform, etc. appearing in the frequency characteristic is a broad waveform, it is difficult to detect the shift of position of the dip waveform, etc. when the amount of the existing specimen is very small.

Another problem of the above-described art method is that, because a variation in incident angle of the electromagnetic wave causes a variation of the dip waveform, etc., a difficulty also arises in the detection when the amount of the existing specimen is very small.

In view of the above-described situations in the art, an object of the present invention is to provide a method of measuring characteristics of a specimen with improved measurement sensitivity and high reproducibility, and further to provide a flat-plate periodic structure that is used to carry out the measuring method.

Solution to Problem

The present invention provides a measuring method comprising the steps of:

holding a specimen on a flat-plate periodic structure, applying a linearly-polarized electromagnetic wave to the periodic structure, detecting the electromagnetic wave scattered forward or backward by the periodic structure, and measuring characteristics of the specimen based on the phenomenon that a dip waveform appearing in a frequency characteristic of the forward-scattered electromagnetic wave or a peak waveform appearing in a frequency characteristic of the backward-scattered electromagnetic wave is changed with the presence of the specimen, wherein the periodic structure is structured such that plural unit structures having the same shape are two-dimensionally and periodically interconnected in a direction of one reference plane, the unit structure has at least one aperture penetrating therethrough in a direction perpendicular to the reference plane, the electromagnetic wave is applied from a direction perpendicular to the reference plane, and the unit structure has a shape that is not mirror-symmetric with respect to an imaginary plane orthogonal to a polarizing direction of the electromagnetic wave.

Preferably, a sectional shape of the unit structure, taken along a polarization plane of the electromagnetic wave, is not mirror-symmetric with respect to the imaginary plane orthogonal to the polarizing direction of the electromagnetic wave.

Preferably, the dip waveform appearing in the frequency characteristic of the forward-scattered electromagnetic wave or the peak waveform appearing in the frequency characteristic of the backward-scattered electromagnetic wave is produced with TE111 mode-like resonance in the periodic structure.

Preferably, a projection is disposed on a principal surface of the unit structure on a side of the unit structure opposite to the side where the specimen is held.

A sectional shape of the aperture of the unit structure, taken along the reference plane, may not be mirror-symmetric with respect to the imaginary plane orthogonal to the polarizing direction of the electromagnetic wave.

In that case, the electromagnetic wave applied to the periodic structure is preferably a plane wave. Furthermore, the electromagnetic wave is preferably applied such that phases of the electromagnetic wave in a principal surface of the periodic structure are substantially the same within at least a range exposed to irradiation with the electromagnetic wave. Still further, the electromagnetic wave is preferably applied such that amplitudes of the electromagnetic wave in a principal surface of the periodic structure are substantially the same within at least a range exposed to irradiation with the electromagnetic wave.

In addition, the present invention provides a flat-plate periodic structure for use in the measuring method described above, wherein the periodic structure is structured such that plural unit structures having the same shape are two-dimensionally and periodically interconnected in a direction of one reference plane, the unit structure has at least one aperture penetrating therethrough in a direction perpendicular to the reference plane, the electromagnetic wave is applied from a direction perpendicular to the reference plane, and the unit structure has a shape that is not mirror-symmetric with respect to an imaginary plane orthogonal to a polarizing direction of the electromagnetic wave.

Advantageous Effects of Invention

According to the present invention, variation in measurement caused by a variation in incident angle of the electromagnetic wave can be suppressed and sensitivity in the measurement of the specimen is improved in comparison with the case where the electromagnetic wave is obliquely incident upon the reference plane since the electromagnetic wave is applied to the flat-plate periodic structure from the direction perpendicular to the reference plane of the periodic structure.

Furthermore, when the aperture of the flat-plate periodic structure used in the present invention is structured such that the dip waveform appearing in the frequency characteristic of the forward-scattered electromagnetic wave or the peak waveform appearing in the frequency characteristic of the backward-scattered electromagnetic wave is produced with the TE111 mode-like resonance in the flat-plate periodic structure, a dip waveform or a peak waveform having a narrower width and being sharper is obtained in comparison with the art in which the electromagnetic wave is obliquely applied to the flat-plate periodic structure. In addition, a frequency shift of the dip waveform or the peak waveform between before and after the specimen is held on the periodic structure becomes larger than in the case where the dip waveform or the peak waveform is produced with the TE110 mode-like resonance in the flat-plate periodic structure. Accordingly, a specimen measuring method with higher measurement sensitivity can be provided.

Moreover, when the sectional shape of the aperture of the unit structure, taken along the reference plane, is not mirror-symmetric with respect to the imaginary plane orthogonal to the polarizing direction of the electromagnetic wave, the dip waveform of a transmittance spectrum (or the peak waveform of a reflectance spectrum) is sharpened and the characteristics of the specimen can be measured with higher sensitivity by employing a plane wave as the electromagnetic wave applied to the periodic structure.

BRIEF DESCRIPTION OF DRAWINGS

FIG. 3 illustrate a unit structure in the one example, illustrated in FIG. 2, of the flat-plate periodic structure according to the present invention. Specifically, FIG. 3(a) is a front view, and FIG. 3(b) is a vertical sectional view.

FIG. 4 are schematic views to explain conditions for an electromagnetic field simulation. Specifically.

FIG. 9 illustrate distribution of electric field vectors obtained with TE111 mode resonance in the periodic structure 1 (made of the unit structure illustrated in FIG. 3), illustrated in FIG. 2, according to the present invention. Specifically.

FIG. 10 illustrate distribution of electric field vectors obtained with TE110 mode resonance in the periodic structure 1 (made of the unit structure illustrated in FIG. 3), illustrated in FIG. 2, according to the present invention. Specifically, FIG. 10(a) illustrates the distribution in the XZ observation plane, FIG. 10(b) illustrates the distribution in the XY observation plane, and FIG. 10(c) illustrates the distribution in the YZ observation plane.

FIG. 13 illustrate a unit structure in one example of the flat-plate periodic structure according to the present invention. Specifically.

FIG. 15 illustrate a unit structure in another example of the flat-plate periodic structure according to the present invention. Specifically.

FIG. 19 illustrate a unit structure in a related-art flat-plate periodic structure. Specifically, FIG. 19(a) is a front view, and FIG. 19(b) is a vertical sectional view.

FIG. 20 illustrate a unit structure in still another example of the flat-plate periodic structure according to the present invention. Specifically.

FIG. 22 illustrate a unit structure in still another example of the flat-plate periodic structure according to the present invention. Specifically, FIG. 22(a) is a front view, and FIG. 22(b) is a vertical sectional view.

FIG. 23 is a graph depicting the frequency characteristic (dotted line) of transmittance obtained with the related-art periodic structure made of the unit structure illustrated in FIG. 19, and a frequency characteristic (solid line) of transmittance obtained with the periodic structure made of the unit structure illustrated in FIG. 22.

FIG. 24 illustrate a unit structure in another example of the related-art flat-plate periodic structure. Specifically.

FIG. 25 illustrate a unit structure in still another example of the flat-plate periodic structure according to the present invention. Specifically.

DESCRIPTION OF EMBODIMENTS

Figure 1:
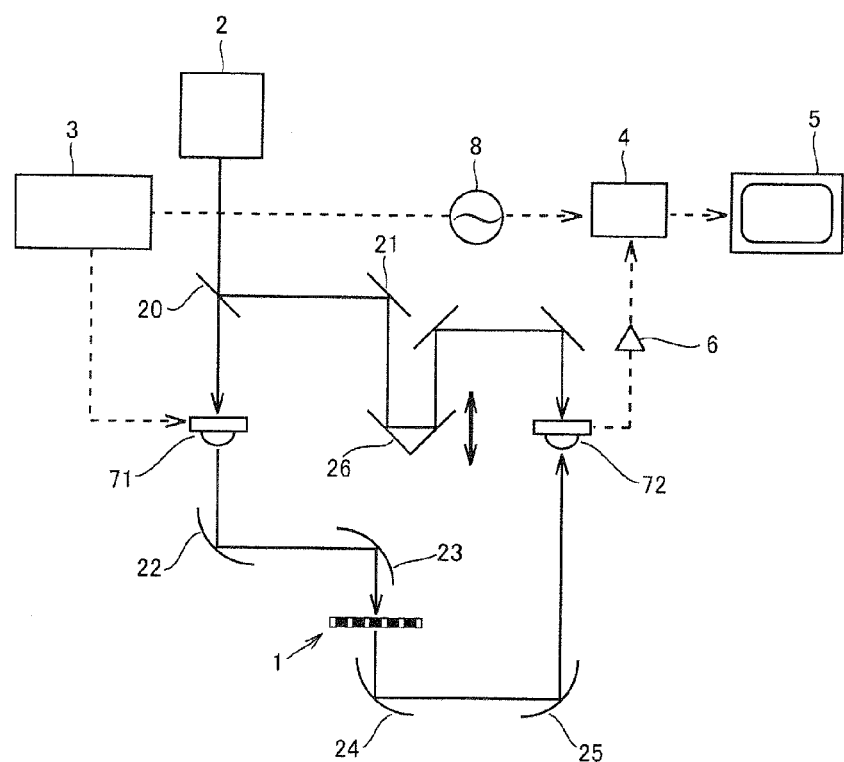
FIG. 1 is a block diagram to explain an outline of a measuring method according to the present invention.

First, an outline of one example of a measuring method according to the present invention will be described below with reference to FIG. 1. FIG. 1 is a block diagram illustrating an overall structure of a measuring apparatus that is used to carry out the measuring method according to the present invention. The measuring apparatus utilizes a pulse of an electromagnetic wave (e.g., a terahertz wave having frequency of 20 GHz to 120 THz), which is generated by irradiating a semiconductor material with a laser beam emitted from a laser 2 (e.g., a short optical pulse laser).

In the configuration of FIG. 1, the laser beam emitted from the laser 2 is branched into two paths by a half mirror 20. One of the branched laser beams is applied to a photoconductive element 71 on the electromagnetic wave generation side, and the other laser beam is applied to a photoconductive element 72 on the reception side via a time delay stage 26 by employing a plurality of mirrors 21 (only one of which is denoted by 21 in FIG. 1 with omission of reference numerals for the other mirrors). The photoconductive elements 71 and 72 can be each prepared using a general photoconductive element obtained by forming, in LT-GaAs (low-temperature grown GaAs), a dipole antenna with a gap portion. The laser 2 may be, e.g., a laser using a solid, such as a fiber type laser or a titanium sapphire laser. The electromagnetic wave can be generated and detected by employing the surface of a semiconductor without an antenna, or an electro-optical crystal such as a ZnTe crystal. A proper bias voltage is applied from a power supply 3 to the gap portion of the photoconductive element 71 on the electromagnetic wave generation side.

The generated electromagnetic wave is converted to a parallel beam through a parabolic mirror 22 and is applied to a flat-plate periodic structure 1 through a parabolic mirror 23. The terahertz wave having transmitted through the flat-plate periodic structure 1 is received by the photoconductive element 72 through parabolic mirrors 24 and 25. An electromagnetic signal received by the photoconductive element 72 is amplified by an amplifier 6 and is then obtained as a time waveform in a lock-in amplifier 4. The received electromagnetic signal is subjected to signal processing, such as Fourier transform, in a PC (personal computer) 5 including calculation means, whereby a transmittance spectrum with the flat-plate periodic structure 1, etc. are calculated. To obtain the time waveform in the lock-in amplifier 4, the bias voltage applied from the power supply 3 to the gap portion of the photoconductive element 71 on the electromagnetic wave generation side is modulated (with an amplitude of 5 V to 30 V) by employing a signal from an oscillator 8. With synchronous detection using the modulated voltage, an S/N ratio can be increased.

The above-described measuring method is a method generally called a terahertz time-domain spectroscopy (THz-TDS).

FIG. 1 illustrates the case where scattering occurs as transmission, i.e., the case of measuring transmittance of an electromagnetic wave. The term "scattering" is used in the present invention as a wide-sense concept including transmission as one form of forward scattering, reflection as one form of backward scattering, etc. Preferably, the term "scattering" implies transmission and reflection. More preferably, the term "scattering" implies transmission in the 0-th order direction and reflection in the 0-th order direction.

In general, given that a lattice spacing of a grating (i.e., an aperture interval in this Description) is d, an incidence angle is i, a diffraction angle is θ, and a wavelength is λ, a spectrum diffracted by the grating can be expressed by:

$$d(\sin i - \sin \theta) = n\lambda \tag{1}$$

The "0-th order" in the term "0-th order direction" implies the case where n in the above formula (1) is 0. Because d and λ cannot take 0, n=0 holds only when sin i−sin θ=0 is satisfied. Thus, the "0-th order direction" implies the direction in which the incidence angle and the diffraction angle are equal to each other, i.e., in which a propagating direction of the electromagnetic wave is not changed.

The electromagnetic wave used in the measuring method according to the present invention is not limited to particular one insofar as it can cause scattering depending on a structural feature specific to the flat-plate periodic structure 1. In practice, the electromagnetic wave may be any of an electric wave, an infrared ray, a visible ray, an ultraviolet ray, an X-ray, and a gamma ray, and its frequency is also not limited to particular one. However, the electromagnetic wave is preferably a terahertz wave having frequency of 1 GHz to 1 PHz and more preferably 20 GHz to 120 THz. In addition, the electromagnetic wave used in the present invention is usually a linearly polarized electromagnetic wave. Practical examples of the electromagnetic wave include a terahertz wave that is generated with the optical rectification effect of an electro-optical crystal, e.g., ZnTe, by employing a short optical pulse laser as a light source, an infrared ray radiated from a high-pressure mercury lamp or a ceramic lamp, visible light emitted from a semiconductor laser, and an electromagnetic wave radiated from a photoconductive antenna.

In the present invention, the expression "measuring characteristics of a specimen" implies, e.g., quantitative measurement of a compound as the specimen and qualitative measurement of a dielectric constant and other properties of the specimen. There are, for example, the case of measuring a minute content of the specimen in, e.g., a solution and the case of identifying the specimen. More specifically, one exemplary method includes the steps of immersing the flat-plate periodic structure in a solution in which the specimen is dissolved, washing solvent and the extra specimen after the specimen has been attached to the surface of the flat-plate periodic structure, drying the flat-plate periodic structure, and measuring characteristics of the specimen by employing a measuring device such as described above. Another exemplary method includes the steps of attaching the specimen to a sheet-like base material made of, e.g., a polymer, holding the flat-plate periodic structure in close contact with the sheet-like base material, and measuring characteristics of the specimen by employing a measuring device such as described above.

The flat-plate periodic structure used in the present invention is structured such that a plurality of unit structures having the same shape are two-dimensionally and periodically interconnected in a direction of one reference plane, and that the unit structure has at least one aperture penetrating therethrough in a direction perpendicular to the reference plane.

Here, the apertures may be all periodically arrayed. As an alternative, some of the apertures may be periodically arrayed and the other apertures may be aperiodically arrayed insofar as the advantageous effects of the present invention are not impaired.

In the present invention, the expression "a plurality of unit structures having the same shape are two-dimensionally and periodically interconnected in a direction of one reference plane" implies a state where the plural unit structures are interconnected such that respective points at identical positions in the individual unit structures (e.g., respective gravity centers of the individual unit structures) are contained in one reference plane. Accordingly, the reference plane is defined by interconnecting arbitrary corresponding points in the individual unit structures constituting the periodic structure. Usually, at least a portion of one principal surface of the unit structure is a flat surface, and the periodic structure is constituted by interconnecting all the unit structures such that the flat surface becomes the reference plane.

Preferably, the flat-plate periodic structure is a quasi-periodic structure or a periodic structure. The term "quasi-periodic structure" implies a structure in which translational symmetry is not held, but the array is orderly kept. Examples of the quasi-periodic structure include a Fibonacci structure as a one-dimensional quasi-periodic structure, and a Penrose structure as a two-dimensional quasi-periodic structure. The term "periodic structure" implies a structure having spatial symmetry such as represented by translational symmetry. The periodic structure is classified into one-dimensional periodic structure, a two-dimensional periodic structure, and a three-dimensional periodic structure depending on the dimension of the symmetry. The one-dimensional periodic structure is, for example, a wire grid structure or a one-dimensional grating. The two-dimensional periodic structure is, for example, a mesh filter or a two-dimensional grating. Of those periodic structures, the two-dimensional periodic structure is preferably employed. In practice, a structure having apertures regularly arrayed in at least one array direction is employed as one example.

Figure 11A:
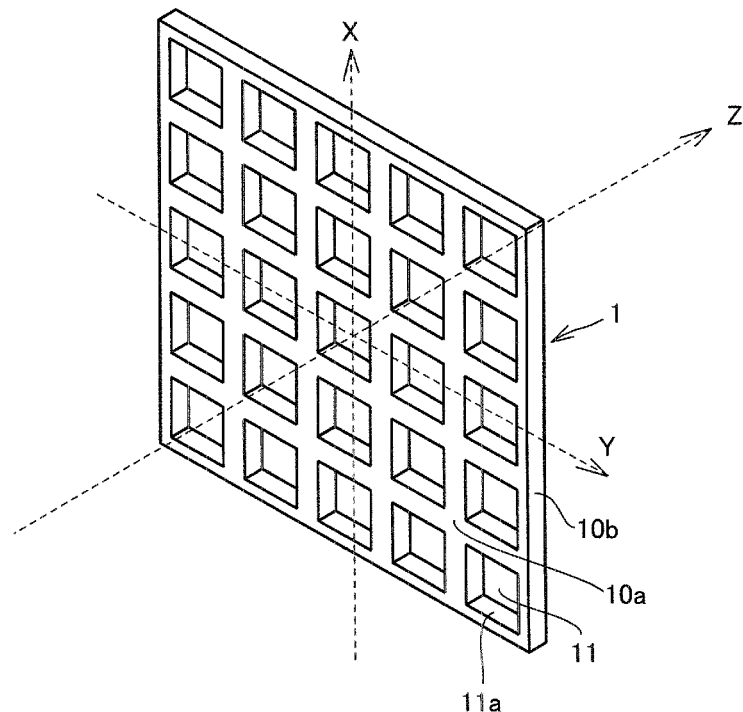
FIG. 11(a)shows apertures are regularly arrayed in the vertical and horizontal directions, while FIG. 11(b) illustrate the lattice spacing of the apertures.
Figure 11B:
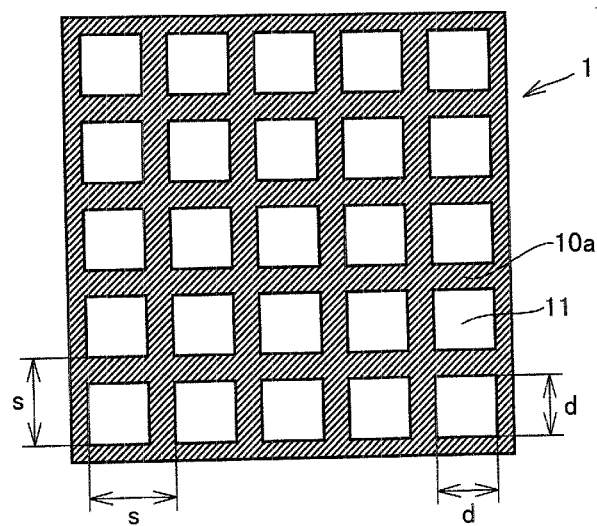
FIG. 11 is a schematic view to explain a (related-art) flat-plate periodic structure.

One example of the related-art two-dimensional periodic structure is a flat-plate structure (also called a lattice structure) in which, as illustrated in FIG. 11(a), apertures are arrayed at constant intervals in a matrix pattern. The periodic structure, illustrated in FIG. 11(a), is structured such that apertures 11, each having a square shape as viewed from the side including a principal surface 10a of the flat structure, are formed at equal intervals in a vertical direction and a horizontal direction in the drawing. It is to be noted that FIGS. 11(a) and 11(b) are illustrated just for explanation, and that a projection or the like provided in the unit structure constituting the flat-plate periodic structure according to the present invention is omitted from the drawings.

In the present invention, the electromagnetic wave is applied to the periodic structure from a direction perpendicular to the reference plane thereof.

The unit structure constituting the periodic structure in the present invention is featured in having a shape that is not mirror-symmetric with respect to an imaginary plane orthogonal to a polarizing direction of the electromagnetic wave.

One example of such a shape of the unit structure is a shape that a sectional shape of the unit structure constituting the flat-plate periodic structure, taken along a polarization plane of the electromagnetic wave, is not mirror-symmetric with respect to the imaginary plane orthogonal to the polarizing direction of the electromagnetic wave. This implies omission of the case where sectional shapes of the unit structure, taken along the polarization plane (including plural planes parallel to the polarization plane) of the electromagnetic wave, are all mirror-symmetric with respect to the imaginary plane. Stated another way, it is required that sectional shapes of at least part of the unit structures in the present invention, taken along the polarization plane (including plural planes parallel to the polarization plane) of the electromagnetic wave, are not mirror-symmetric with respect to the imaginary plane.

In practice, the above-mentioned shape is obtained, for example, with the case where a thickness of the unit structure is not uniform and is not symmetrically distributed with respect to the imaginary plane. Here, the "thickness of the unit structure" implies the length of the unit structure in the direction perpendicular to the above-described reference plane of the periodic structure. A more specific example is the case where the unit structure includes a projection in its part. When the specimen is held over one entire surface of the periodic structure (unit structure), the surface of the unit structure on which the specimen is held is preferably formed as a flat surface and the projection is preferably disposed only on a principal surface of the unit structure on one side of the unit structure opposite to the other side where the specimen is held, so that a variation does not occur in measurement results depending on positions where the specimen is held.

Furthermore, the above-described shape of the unit structure is preferably such a shape as producing TE111 mode-like resonance upon irradiation with the electromagnetic wave when the aperture of each unit structure is regarded as a waveguide. Herein, the term "TE111 mode-like resonance" includes resonance in the TE111 mode and resonance in a mode analogous to the TE111 mode. The aperture having such a shape as producing the TE111 mode-like resonance is advantageous in that a sharp dip waveform can be obtained in the frequency characteristic of the forward-scattered electromagnetic wave, or that a sharp peak waveform can be obtained in the frequency characteristic of the backward-scattered electromagnetic wave. Another advantage is that, since a frequency shift amount of the dip waveform or the peak waveform is increased between before and after the specimen is held on the periodic structure, sensitivity in measurement of the specimen can be improved.

Herein, the term "dip waveform" implies a waveform in a valley-shaped (downward-convex) portion, which partly appears in a frequency characteristic (e.g., a transmittance spectrum) with the flat-plate periodic structure in a frequency range where a ratio of the detected electromagnetic wave to the applied electromagnetic wave (e.g., a transmittance of the electromagnetic wave) is relatively increased. Also, the term "peak waveform" implies a waveform in a mountain-shaped (upward-convex) portion, which partly appears in a frequency characteristic (e.g., a reflectance spectrum) with the flat-plate periodic structure in a frequency range where a ratio of the detected electromagnetic wave to the applied electromagnetic wave (e.g., a reflectance of the electromagnetic wave) is relatively reduced.

When the unit structure has such a shape as producing the TE111 mode-like resonance, the aperture shape is preferably, for example, a shape that does not produce the TE110 mode-like resonance upon irradiation with the electromagnetic wave when each aperture is regarded as a waveguide. Herein, the term "TE110 mode-like resonance" includes resonance in the TE110 mode and resonance in a mode analogous to the TE110 mode. The TE110 mode-like resonance is not produced when a projection image of the aperture projected to the above-described reference plane or a sectional shape (two-dimensional shape) of the aperture taken along the reference plane is mirror-symmetric with respect to the imaginary plane perpendicular to the polarizing direction of the electromagnetic wave. With the TE110 mode-like resonance being not produced, it is possible to reduce a factor causing noise in the measurement based on the dip waveform or the peak waveform that is generated with the TE111 mode-like resonance.

Depending on the type of specimen, however, it may be desirable to form the aperture in such a shape as producing the TE110 mode-like resonance as described below, and to perform the measurement of the specimen based on both the dip waveform or the peak waveform that is generated with the TE110 mode-like resonance, and the dip waveform or the peak waveform that is generated with the TE111 mode-like resonance. Such a measuring method is also involved within the scope of the present invention.

Another example of the shape of the unit structure is the case where a two-dimensional shape of the aperture of the unit structure (i.e., a sectional shape taken along a reference plane) is not mirror-symmetric with respect to the imaginary plane perpendicular to the polarizing direction of the electromagnetic wave. The term "reference plane" is used in the same meaning as that described above, and it implies a plane containing the direction in which the unit structures are arrayed. In that case, the TE110 mode-like resonance is produced upon irradiation with the electromagnetic wave when each aperture is regarded as a waveguide. Examples of the two-dimensional shape of the aperture, which produces the TE110 mode-like resonance, include a trapezoidal shape, a convex shape, a concave shape, a polygonal shape other than a regular polygonal shape, a regular polygonal shape having an odd number of angles (e.g., a regular triangular shape or a regular pentagonal shape), and a star-like shape.

The electromagnetic wave applied to the periodic structure made of the unit structure that has the aperture producing the TE110 mode-like resonance is preferably a plane wave. More specifically, the electromagnetic wave emitted from the light source is preferably applied to the periodic structure after being converted to a plane wave (parallel light) through a parabolic mirror, a lens, etc.

Moreover, preferably, phases of the electromagnetic wave in the principal surface of the periodic structure are substantially the same within at least a range exposed to the irradiation with the electromagnetic wave. Stated another way, preferably, phases of the electromagnetic wave are substantially the same at all positions (points) in a portion of the principal surface of the periodic structure, which portion is exposed to the irradiation with electromagnetic wave. The reason is that, the dip waveform appearing in the transmittance spectrum (or the peak waveform appearing in the reflectance spectrum) is sharpened with the phases of the electromagnetic wave being the same, and that the characteristics of the specimen can be measured with higher sensitivity.

In addition, preferably, amplitudes of the electromagnetic wave in the principal surface of the periodic structure are substantially the same within at least the range exposed to the irradiation with electromagnetic wave. The reason is that, with the amplitudes of the electromagnetic wave being the same, the dip waveform appearing in the transmittance spectrum (or the peak waveform appearing in the reflectance spectrum) is sharpened, and that the characteristics of the specimen can be measured with higher sensitivity.

Furthermore, a proportion of change which is caused by the presence of the specimen, in the dip waveform appearing in the frequency characteristic of the forward-scattered electromagnetic wave or in the peak waveform appearing in the frequency characteristic of the backward-scattered electromagnetic wave can be increased, for example, by covering the surface of a portion of the periodic structure (unit structure), in which the intensity of an electric field generated by the TE111 mode-like resonance, the TE110 mode-like resonance, etc. is relatively strong, with a substance having high associativity to the specimen such that the specimen is selectively held on the surface of such a portion.

The size of the aperture of the unit structure is designed, as appropriate, depending on the measuring method, the material characteristics of the flat-plate periodic structure, the frequency of the electromagnetic wave used, etc. It is hence difficult to generalize the range of the aperture size. However, when the forward-scattered electromagnetic wave is detected, it is preferable in the flat-plate periodic structure 1, in which the apertures are regularly arrayed in the vertical and horizontal directions as illustrated in FIG. 11(a), that the lattice spacing of the apertures, denoted by s in FIG. 11(b), is not less than 1/10 and not more than 10 times the wavelength of the electromagnetic wave used in the measurement. If the lattice spacing s of the apertures is outside the above-mentioned range, the electromagnetic wave may be less apt to scatter in some cases. Furthermore, it is preferable that the opening size of the aperture, denoted by d in FIG. 11(b), is not less than 1/10 and not more than 10 times the wavelength of the electromagnetic wave used in the measurement. If the opening size d of the aperture is outside the above-mentioned range, the intensity of the transmitted (forward-scattered) electromagnetic wave may be so weakened as to cause a difficulty in detecting the signal in some cases.

The average thickness of the flat-plate periodic structure is also designed, as appropriate, depending on the measuring method, the material characteristics of the flat-plate periodic structure, the frequency of the electromagnetic wave used, etc. It is hence difficult to generalize the range of average thickness of the flat-plate periodic structure. However, when the forward-scattered electromagnetic wave is detected, the average thickness of the flat-plate periodic structure is preferably not more than several times the wavelength of the electromagnetic wave used in the measurement. If the average thickness of the structure exceeds the above-mentioned range, the intensity of the forward-scattered electromagnetic wave may be so weakened as to cause a difficulty in detecting the signal in some cases.

In the present invention, the specimen can be held on the flat-plate periodic structure by optionally employing various known methods. For example, the specimen may be directly attached to the flat-plate periodic structure or may be attached to the flat-plate periodic structure with, e.g., a support film interposed therebetween. However, the specimen is preferably directly attached to the surface of the flat-plate periodic structure from the viewpoint of improving measurement sensitivity and reducing variations in the measurement, thereby performing the measurement with higher reproducibility.

Direct attachment of the specimen to the flat-plate periodic structure includes not only the case where chemical bonding, for example, is directly formed between the surface of the flat-plate periodic structure and the specimen, but also the case where a flat-plate periodic structure having the surface to which a host molecule is bonded in advance is employed and the specimen is bonded to the host molecule. Examples of the chemical bonding include covalent bonding (e.g., covalent bonding between a metal and a thiol group), Van der Waals bonding, ionic bonding, metal bonding, and hydrogen bonding. Of those examples, the valence bonding is preferable. The term "host molecule" implies a molecule to which the specimen can specifically be bonded. Combinations of the host molecule and the specimen are, for example, an antigen and an antibody, a sugar chain and a protein, a lipid and a protein, a low-molecule compound (ligand) and a protein, a protein and a protein, as well as a single strand DNA and a single strand DNA.

When the specimen is directly attached to the flat-plate periodic structure, it is preferable to use such a flat-plate periodic structure that the surface of at least a part thereof is formed by a conductor. The expression "the surface of at least a part of the flat-plate periodic structure 1" implies the surface of a part of any of the principal surface 10a, a side surface 10b of the flat-plate periodic structure 1, and a side surface 11a of the aperture, which are illustrated in FIG. 11(a).

Herein, the term "conductor" implies an object (substance) capable of conducting electricity therethrough, and it includes not only a metal, but also a semiconductor. Examples of the metal include a metal capable of being bonded to a functional group, such as a hydroxy group, a thiol group, or a carboxyl group, of a compound containing that functional group, a metal capable of coating a functional group, such as a hydroxy group or an amino group, on the surface of the metal, and an alloy of those metals. Practical examples of the metals are gold, silver, copper, iron, nickel, chromium, silicon, germanium, etc. Of those examples, gold, silver, copper, nickel, and chromium are preferable. Gold is more preferable. Using gold or nickel is advantageous in that, particularly when the specimen contains a thiol group (—SH group), the thiol group can be bonded to the surface of the flat-plate periodic structure. Furthermore, using nickel is advantageous in that, particularly when the specimen contains a hydroxy group (—OH) or a carboxyl group (—COOH), such a functional group can be bonded to the surface of the flat-plate periodic structure. Moreover, examples of the semiconductor include a group IV semiconductor (e.g., Si or Ge), and compound semiconductors, e.g., a group II-VI semiconductor (e.g., ZnSe, CdS or ZnO), a group III-V semiconductor (e.g., GaAs, InP or GaN), a group IV compound semiconductor (e.g., SiC or SiGe), and a group I-III-VI semiconductor (e.g., $CuInSe_2$), as well as organic semiconductors.

The attachment of the specimen to the flat-plate periodic structure with, e.g., a support film interposed therebetween can be performed, for example, by a method of sticking a support film made of, e.g., a polyamide resin to the surface of the flat-plate periodic structure and attaching the specimen to the support film, or by a method of using a gas-tight or liquid-tight container instead of the support film and measuring a fluid or a substance dispersed in a fluid.

With the measuring method according to the present invention, the characteristics of the specimen are measured on the basis of at least one parameter relating to the frequency characteristic of the electromagnetic wave dispersed by the flat-plate periodic structure, the frequency characteristic being determined as described above. The characteristics of the specimen can be measured, for example, on the basis of a phenomenon that, when the flat-plate periodic structure 1 is employed, the dip waveform appearing in the frequency characteristic of the forward-dispersed (transmitted) electromagnetic wave or the peak waveform appearing in the frequency characteristic of the backward-dispersed (reflected) electromagnetic wave is changed with the presence of the specimen.

Figure 2:
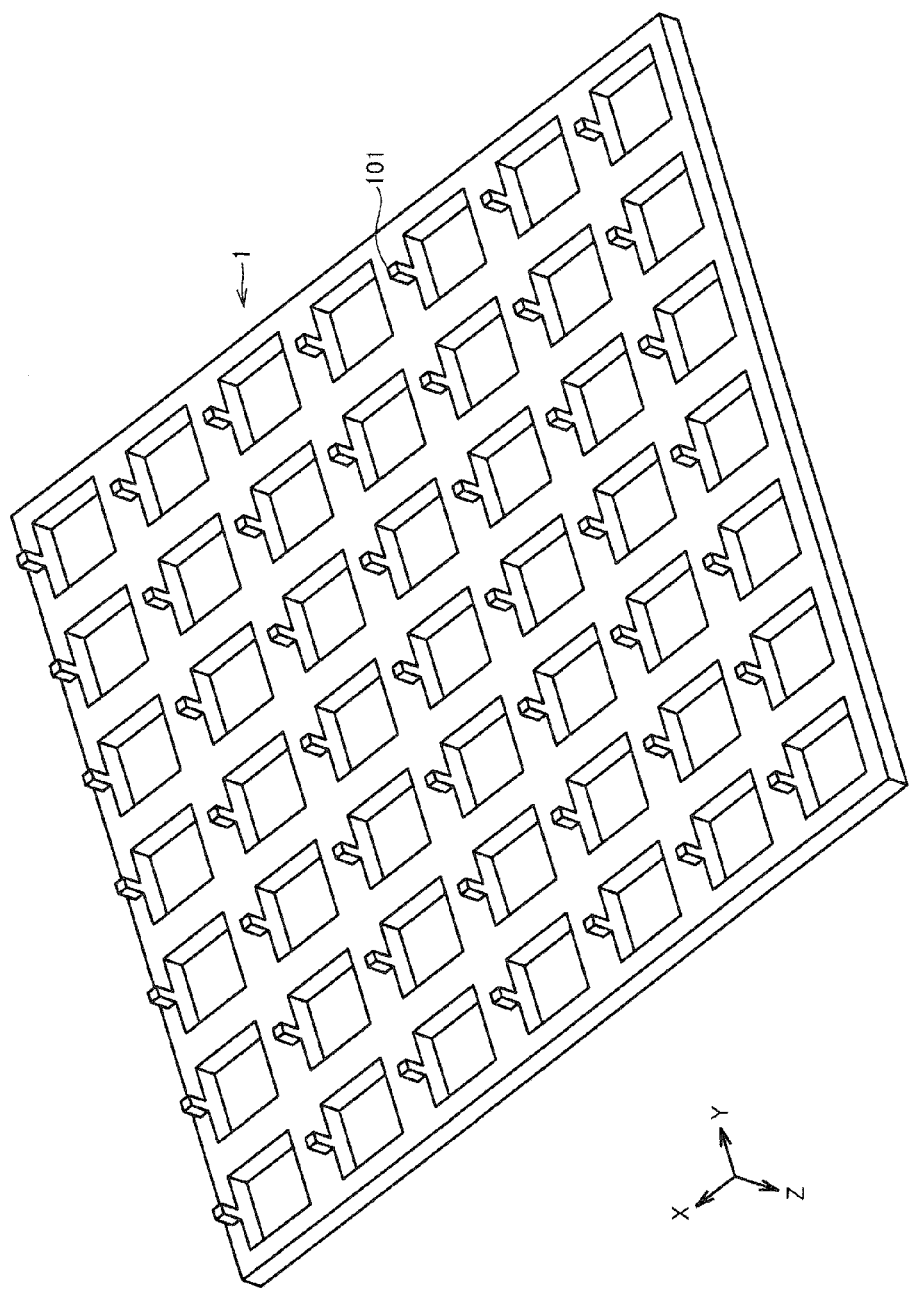
FIG. 2 is a perspective view of one example of a flat-plate periodic structure according to the present invention.

An electromagnetic field simulation with the FDTD (Finite-difference time-domain) method was carried out, by way of example, on the flat-plate periodic structure including, as illustrated in FIGS. 2 and 3, a projection 101 added to a portion of each of unit structures constituting the periodic structure 1. The operation of the present invention is described below on the basis of the simulation result.

FIG. 2 is a perspective view of the flat-plate periodic structure 1 according to the present invention. FIG. 3 illustrates a unit structure in one example, illustrated in FIG. 2, of the flat-plate periodic structure according to the present invention. Specifically, FIG. 3(a) is a front view, and FIG. 3(b) is a vertical sectional view. The flat-plate periodic structure has such an entire shape that through-holes (apertures), each having a square shape with dimensions of 180×180 μm, are formed in an Au-made flat plate with a thickness of 60 μm, and that the apertures are periodically arrayed in a square lattice pattern at a pitch of 254 μm with a unit structure including the projection 101. The projection 101 has a rectangular parallelepiped shape with dimensions of 20 μm long× 20 μm wide×40 μm thick.

In FIGS. 2 and 3, Z denotes the propagating direction of the electromagnetic wave used in the irradiation, X denotes the polarizing direction of the electromagnetic wave (i.e., the direction of an electric field), and Y denotes the direction of a magnetic field (i.e., the direction perpendicular to X and Z) (these definitions are similarly applied to the other drawings representing the present invention).

Figure 4A:
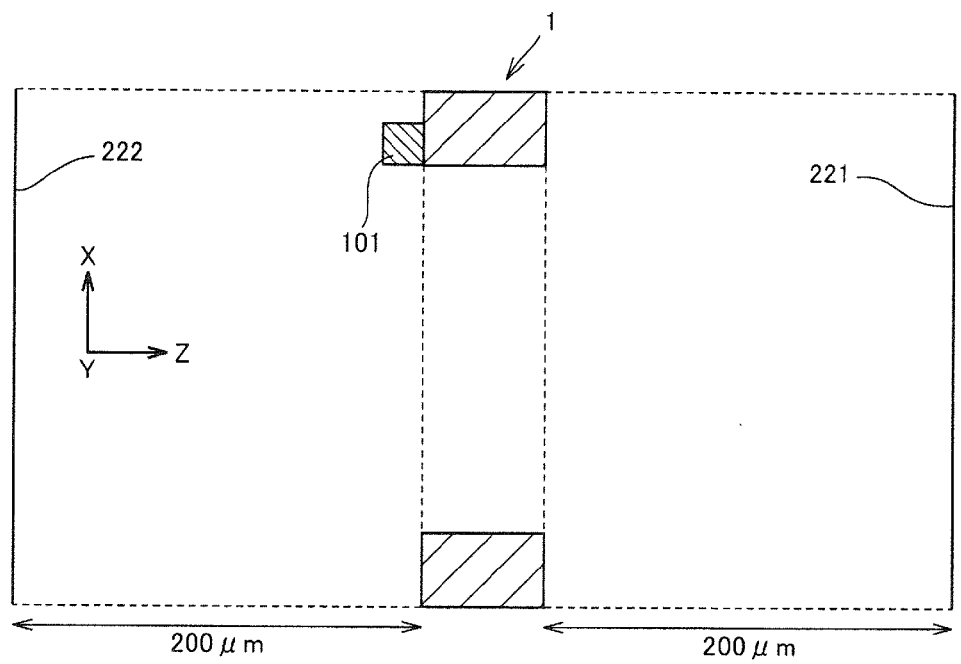
FIG. 4(a) is a vertical sectional view.
Figure 4B:
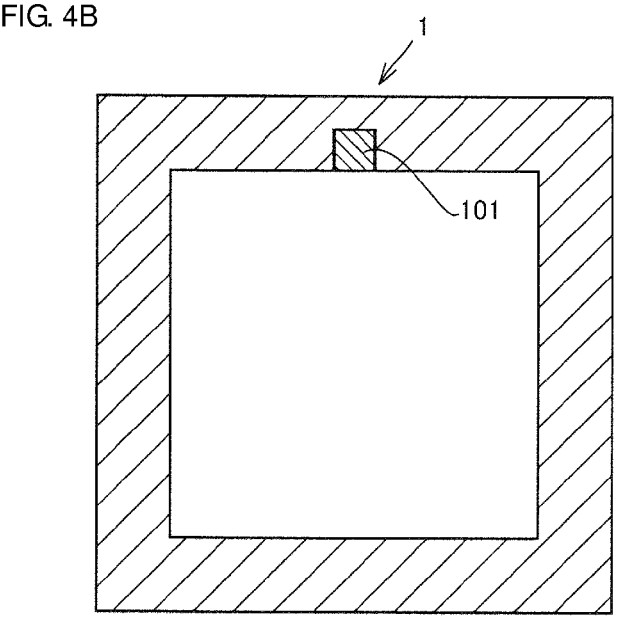
FIG. 4(b) is a front view.

Conditions for an electromagnetic field simulation will be described below with reference to FIG. 4. The conditions for the electromagnetic field simulation in accordance with the FDTD method were set such that, as illustrated in FIG. 2, one principal surface of the periodic structure 1 including the projection 101 for each unit structure (254×254×60 μm) was an incident surface, the other principal surface of the periodic structure 1 opposite to the one principal surface was a detection surface, and other surfaces thereof were periodic boundaries. Furthermore, the unit structure was divided into basic units, i.e., unit cells each having a size of 5 μm in all the XYZ directions. Moreover, the periodic structure was made of Au.

The electromagnetic wave was applied to the periodic structure such that a plane wave (linearly polarized wave) was perpendicularly incident upon the principal surface of the periodic structure, and that one side (edge) of the aperture on the side of the unit structure where the projection 101 is additionally provided was positioned orthogonal to the polarizing direction X of the incident electromagnetic wave (i.e., the direction of an electric field). Furthermore, detection of the wave scattered from the flat-plate periodic structure was made by detecting forward scattering (i.e., the wave having transmitted through the structure), and the transmitted electromagnetic wave was detected at a detection surface 221 disposed on the side opposite to a source of the plane wave. The distance between the periodic structure 1 and the detection surface 221 was set to 200 μm.

Figure 5:
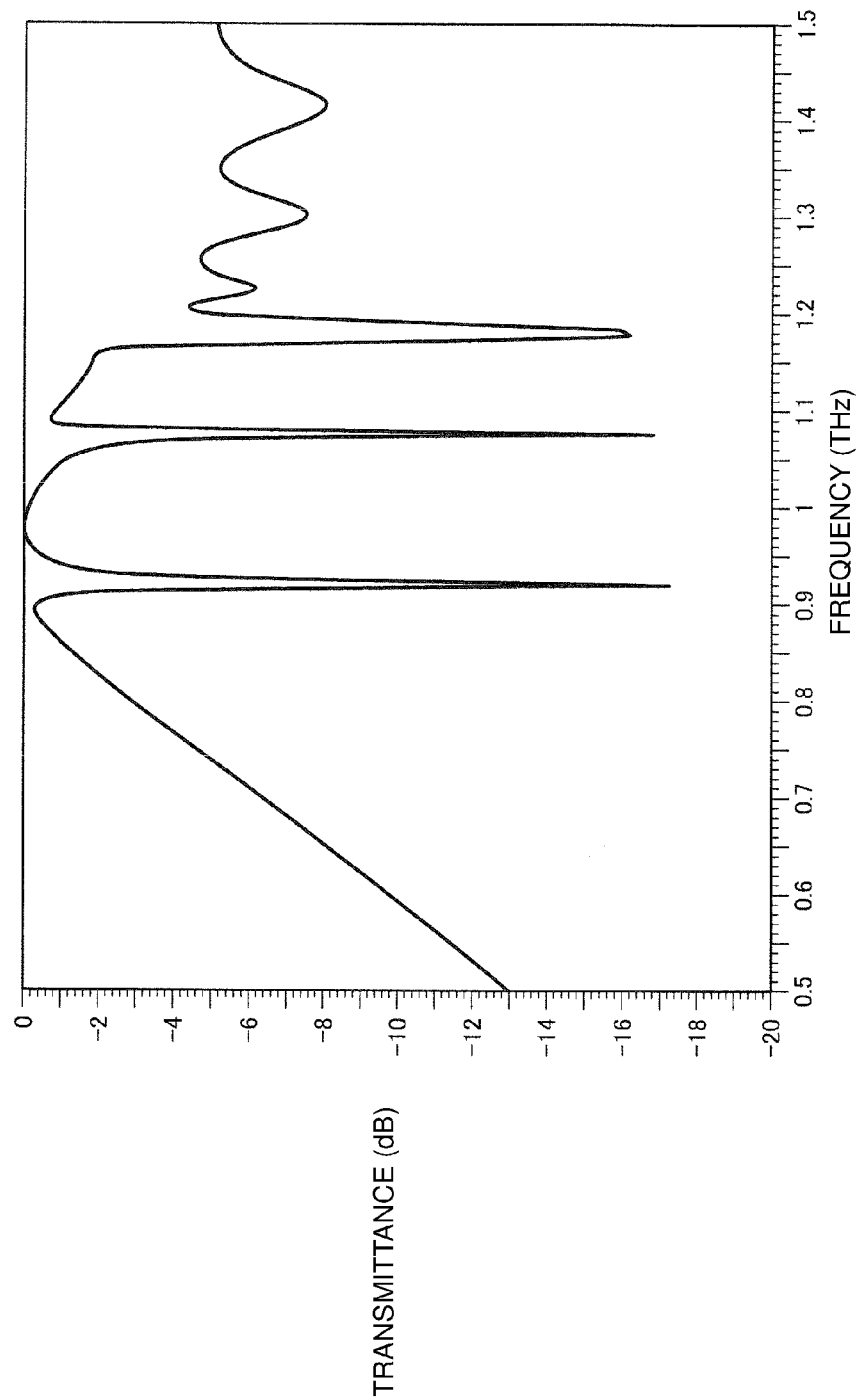
FIG. 5 is a graph depicting a frequency characteristic (simulation calculation) of transmittance obtained with the periodic structure 1, illustrated in FIG. 2, according to the present invention.
Figure 6:
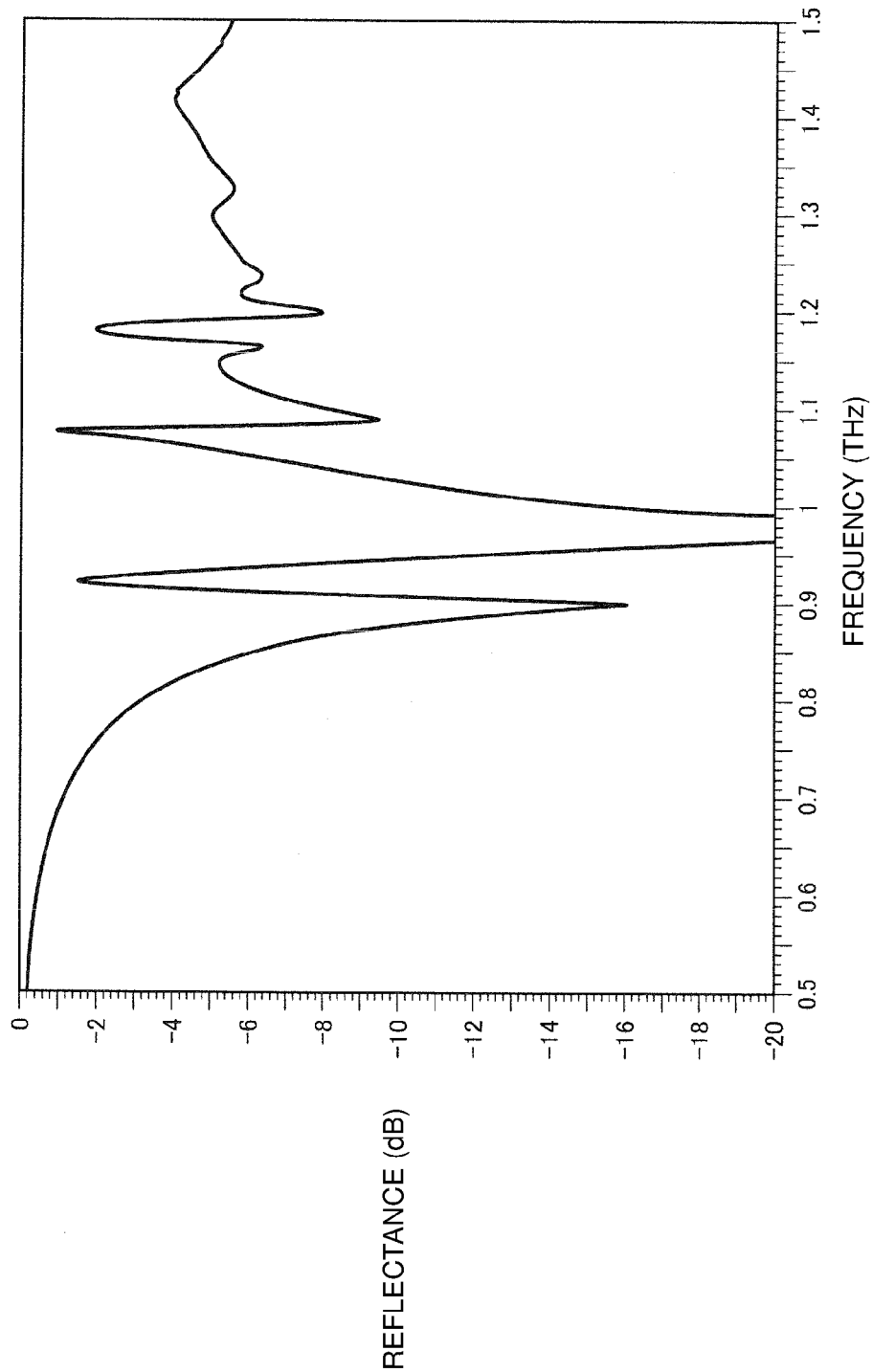
FIG. 6 is a graph depicting a frequency characteristic (simulation calculation) of reflectance obtained with the periodic structure 1, illustrated in FIG. 2, according to the present invention.

FIG. 5 is a graph depicting a frequency characteristic of transmittance obtained with the periodic structure 1, illustrated in FIG. 2, according to the present invention. Similarly, an electromagnetic field simulation was performed on the case where the backward-scattered (reflected) electromagnetic wave was detected at a detection surface 222 disposed on the same side as the source of the plane wave. FIG. 6 depicts a frequency characteristic of reflectance obtained with the periodic structure 1, illustrated in FIG. 2, according to the present invention.

As seen from FIGS. 5 and 6, at frequencies near 0.92 THz and 1.17 THz, there appear respectively two dip waveforms of the frequency characteristic (transmittance spectrum) of the forward-scattered electromagnetic wave and two peak waveforms of the frequency characteristic (reflectance spectrum) of the backward-scattered electromagnetic wave. The dip waveform (or the peak waveform) on the higher frequency side is produced with the TE111 mode resonance, and the dip waveform (or the peak waveform) on the lower frequency side is produced with the TE110 mode resonance. The present invention is featured in improving sensitivity in the measurement of the specimen by measuring the former waveform.

Figure 7:
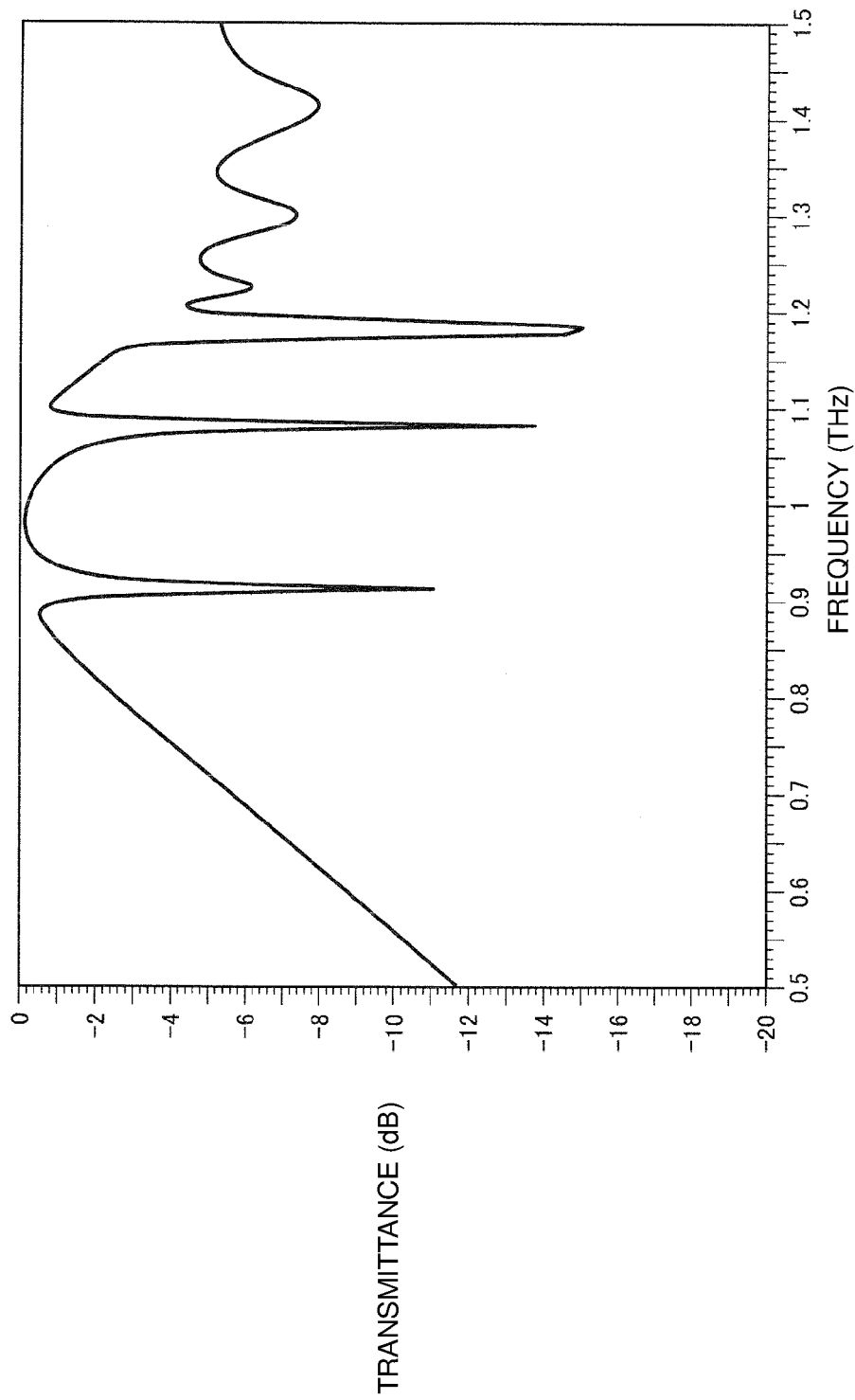
FIG. 7 is a graph depicting a frequency characteristic of transmittance obtained with the periodic structure 1, illustrated in FIG. 2, according to the present invention.
Figure 8:
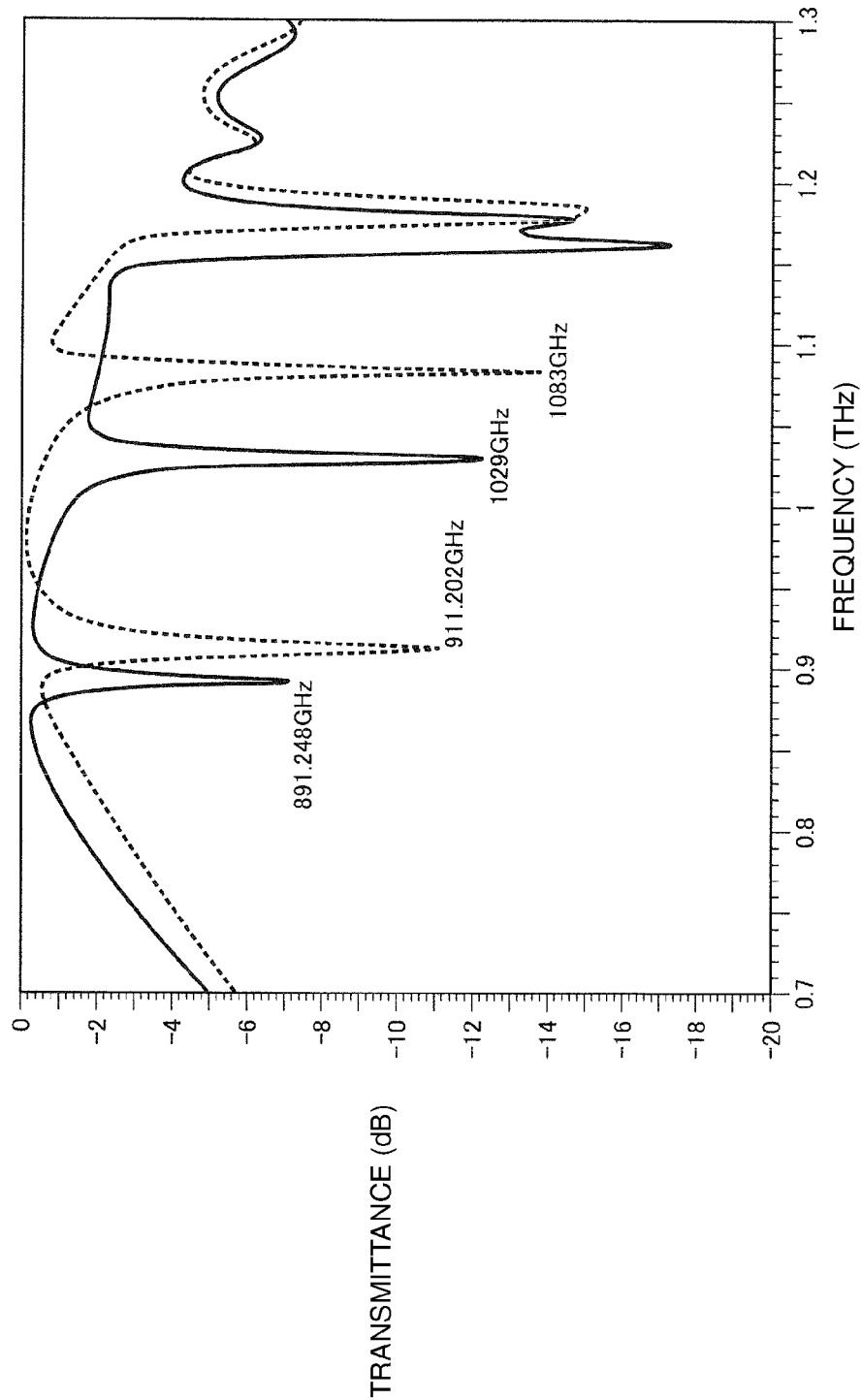
FIG. 8 is a graph depicting frequency characteristics of transmittance obtained with the periodic structure 1, illustrated in FIG. 2, according to the present invention before and after close attachment of a polyethylene film. A dotted line represents the frequency characteristic, which is the same as that depicted in FIG. 7, before the close attachment of the polyethylene film, and a solid line represents the frequency characteristic after the close attachment of the polyethylene film.

FIG. 7 depicts a frequency characteristic of transmittance obtained with the periodic structure 1, illustrated in FIG. 2, according to the present invention. FIG. 8 depicts frequency characteristics of transmittance obtained with the periodic structure 1, illustrated in FIG. 2, according to the present invention before and after close attachment of a polyethylene film (specimen). A dotted line represents the frequency characteristic, which is the same as that depicted in FIG. 7, before the close attachment of the polyethylene film, and a solid line represents the frequency characteristic after the close attachment of the polyethylene film. It is to be noted that the polyethylene film has a thickness of 10 μm and a dielectric constant of 2.4, tan δ=0.01.

As depicted in FIG. 8, the dip waveform on the higher frequency side, which is produced with the TE111 mode resonance, exhibits a frequency change of 54 GHz (1083-1029 GHz) before and after the close attachment of the polyethylene film, and the dip waveform on the lower frequency side, which is produced with the TE110 mode resonance, exhibits a frequency change of about 20 GHz (911.202-891.248 GHz). As seen from those results, the measurement of the specimen can be performed with higher sensitivity by employing the dip waveform on the higher frequency side produced with the TE111 mode resonance than by employing the dip waveform on the lower frequency side produced with the TE110 mode resonance.

Figure 9C:
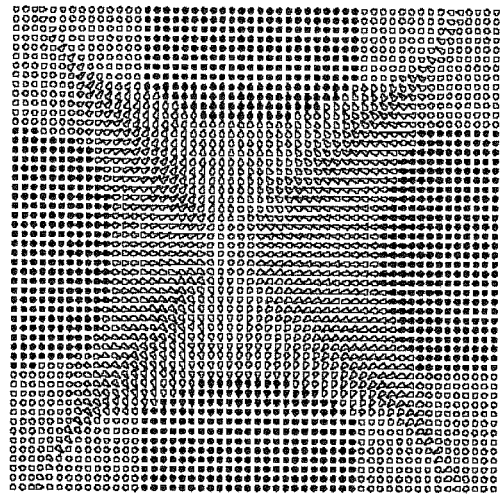
FIG. 9(c) illustrates the distribution in a YZ observation plane.
Figure 9B:
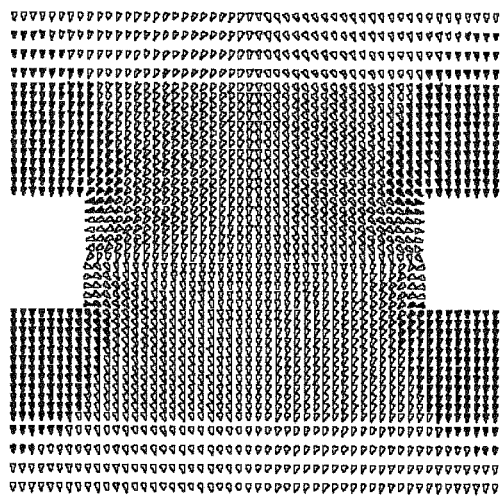
FIG. 9(b) illustrates the distribution in an XY observation plane.
Figure 9A:
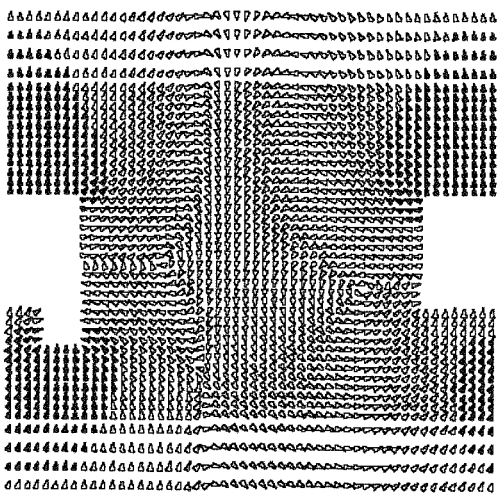
FIG. 9(a) illustrates the distribution in an XZ observation plane.

FIG. 9 illustrates a distribution of electric field vectors obtained with the TE111 mode resonance in the periodic structure 1 (made of the unit structure illustrated in FIG. 3), illustrated in FIG. 2, according to the present invention. Specifically, FIG. 9(a) illustrates the distribution in an XZ observation plane, FIG. 9(b) illustrates the distribution in an XY observation plane, and FIG. 9(c) illustrates the distribution in a YZ observation plane. FIG. 10 illustrates a distribution of electric field vectors obtained with the TE110 mode resonance in the periodic structure 1 (made of the unit structure illustrated in FIG. 3), illustrated in FIG. 2, according to the present invention. Specifically, FIG. 10(a) illustrates the distribution in the XZ observation plane, FIG. 10(b) illustrates the distribution in the XY observation plane, and FIG. 10(c) illustrates the distribution in the YZ observation plane. In FIGS. 9 and 10, a direction of the most sharpened corner (i.e., an apex having the smallest angle) of each triangle denotes a direction of the electric field vector. A black triangle represents a portion where the electric field vector is comparatively large (i.e., the intensity of electric field is relatively strong), and a white triangle represents a portion where the electric field vector is comparatively small.

As seen from FIGS. 9 and 10, the distribution of electric field (FIG. 9) obtained with TE111 mode resonance contains a distribution not so uniform as compared with the distribution of electric field (FIG. 10) obtained with TE110 mode resonance in the Z-direction (i.e., in the propagating direction of the electromagnetic wave) (see particularly FIGS. 9(a) and 10(a)).

Figure 12:
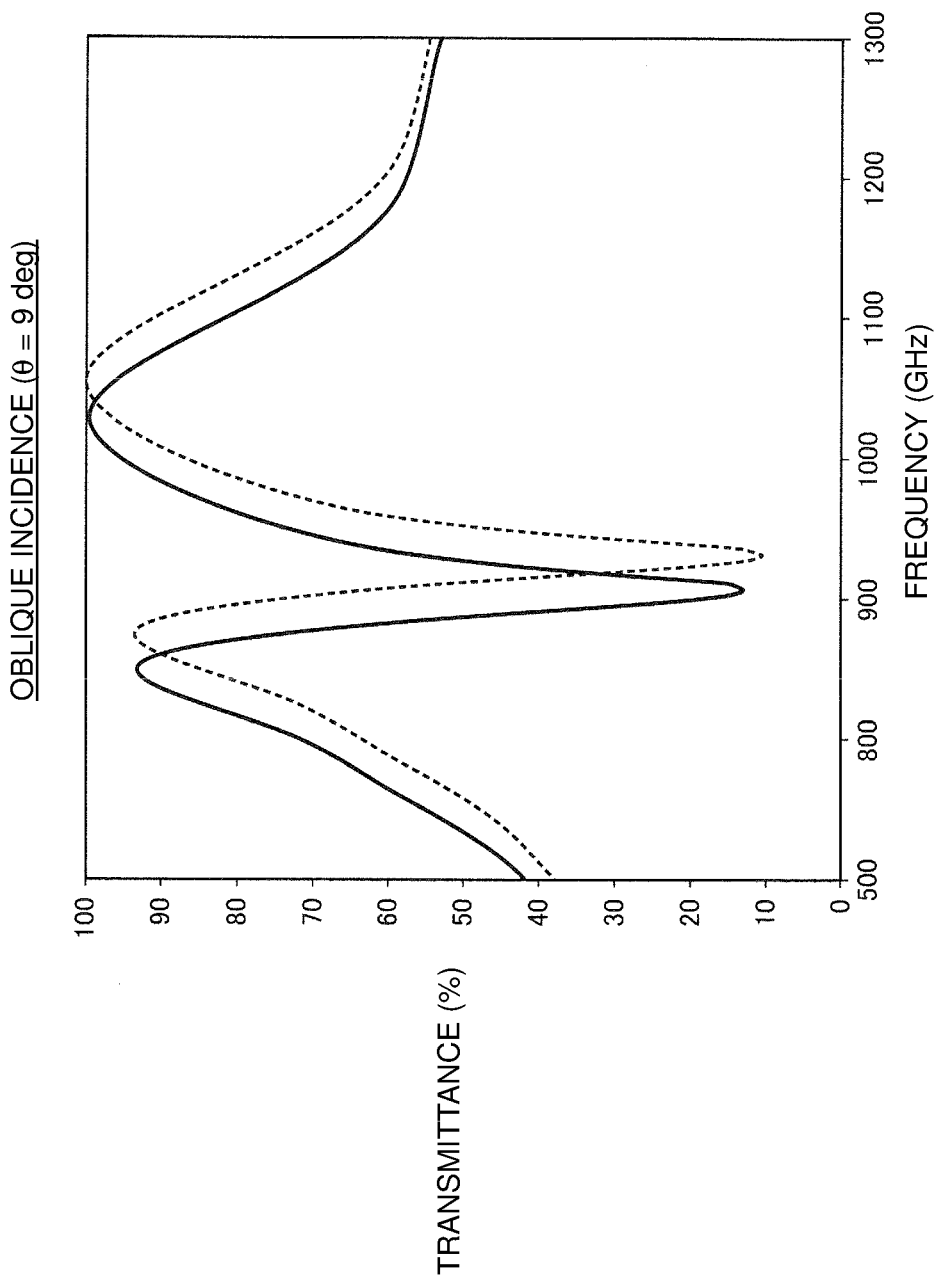
FIG. 12 is a graph depicting frequency characteristics of transmittance obtained with a related-art measuring method before and after close attachment of a polyethylene film.

For the purpose of comparison, a frequency characteristic of transmittance was measured using the related-art periodic structure, illustrated in FIG. 11, when the periodic structure 1 was arranged obliquely to the direction in which the electromagnetic wave was applied. The periodic structure 1 was set in such a state that it was rotated by 9° about a Y-axis in FIG. 11 from a position where the principal surface of the periodic structure 1 was perpendicular to the propagating direction Z of the electromagnetic wave. FIG. 12 depicts the transmittance before close attachment of a polyethylene film by a solid line, and the transmittance after the close attachment of the polyethylene film by a dotted line. In that case, a frequency change of the dip waveform was 21 GHz (931-910 GHz). Note that simulation calculation was executed in a similar manner to the simulation calculation in accordance with the above-described FDTD method except for not including the projection.

EXAMPLES

The present invention will be described in detail below in connection with reference to EXAMPLES, but the present invention is not limited to the following EXAMPLES.

Example 1

Figure 13B:
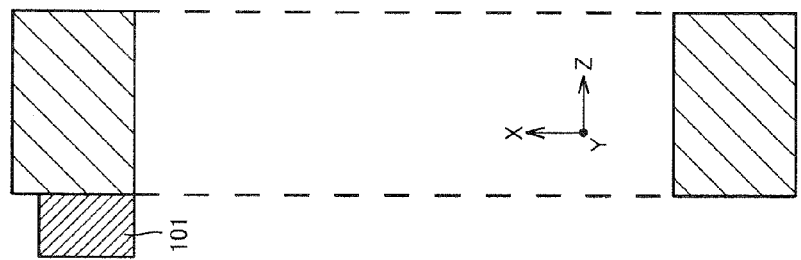
FIG. 13(b) is a vertical sectional view.
Figure 13A:
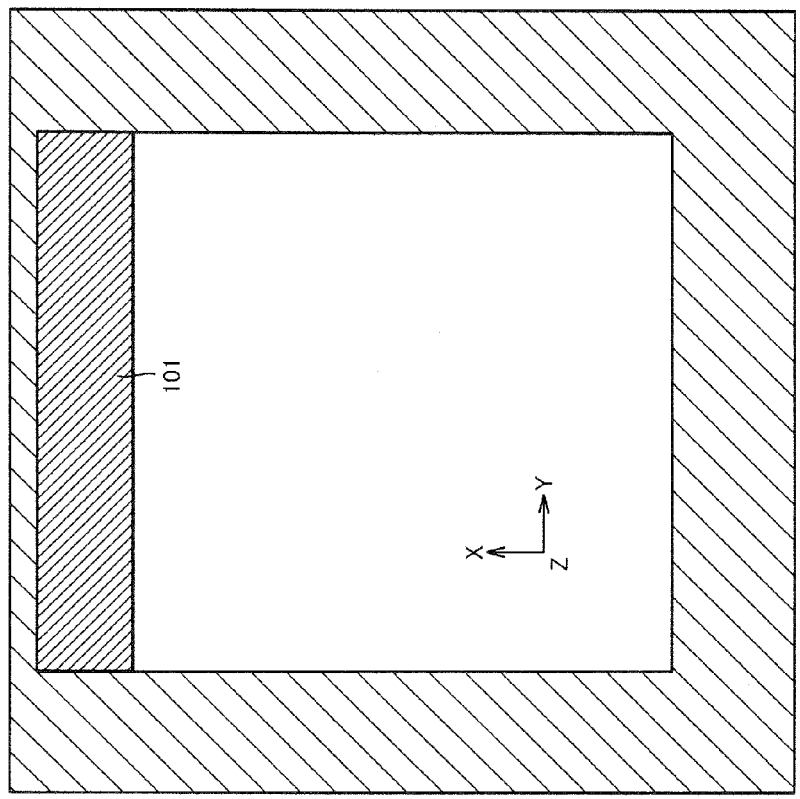
FIG. 13(a) is a front view.
Figure 14:
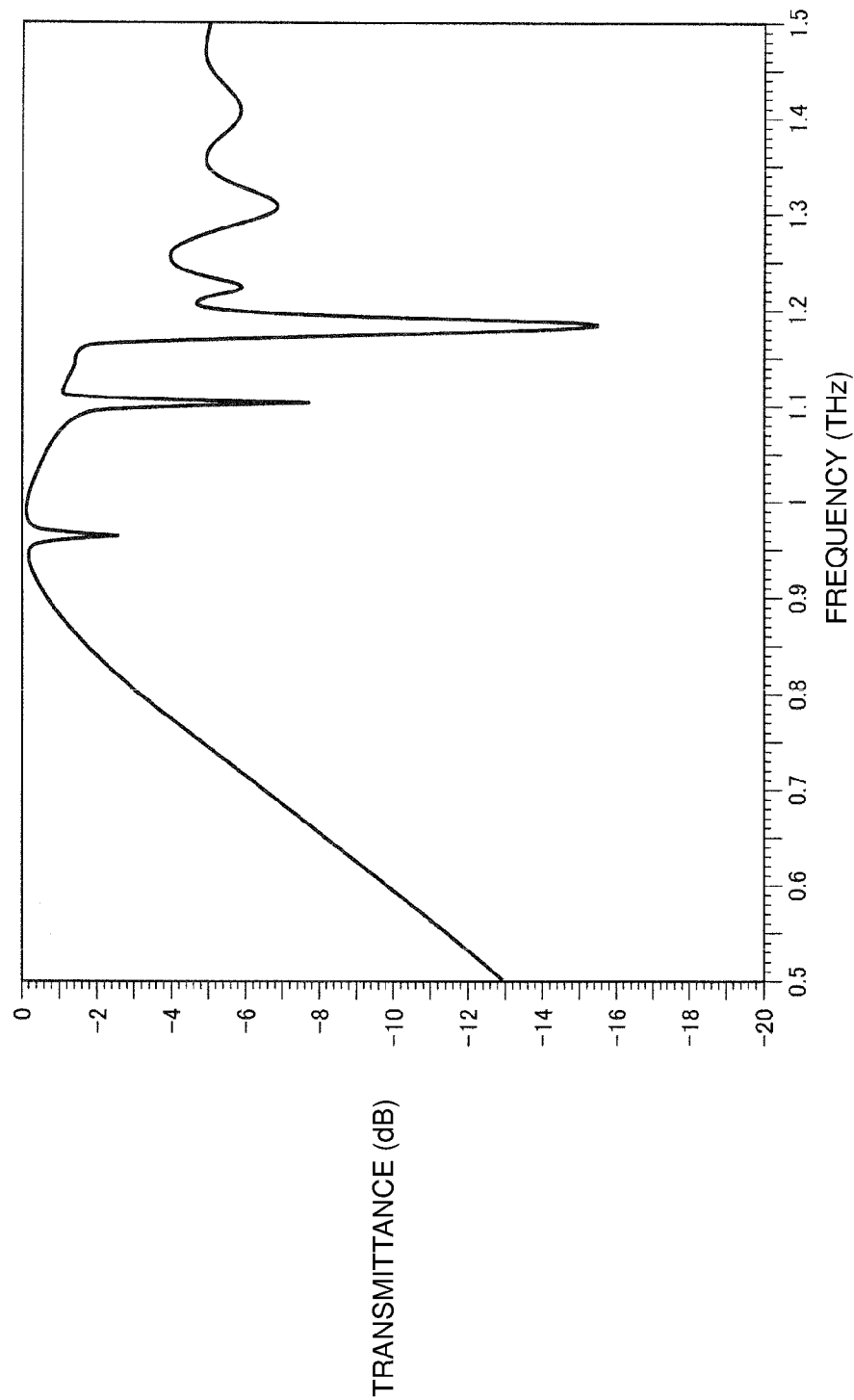
FIG. 14 is a graph depicting a frequency characteristic of transmittance obtained with the periodic structure made of the unit structure illustrated in FIG. 13.

Simulation calculation in accordance with the FDTD method was executed in a similar manner to that described above except for using a flat-plate periodic structure according to the present invention, the flat-unit periodic structure being made of a unit structure (having a large projection) as illustrated in FIG. 13. FIG. 14 depicts a frequency characteristic of transmittance obtained with that simulation calculation. The dip waveform produced with the TE111 mode resonance appears near 1.1 THz. The dip waveform appearing near 0.96 THz is produced with the TE110 mode resonance.

Figure 15B:
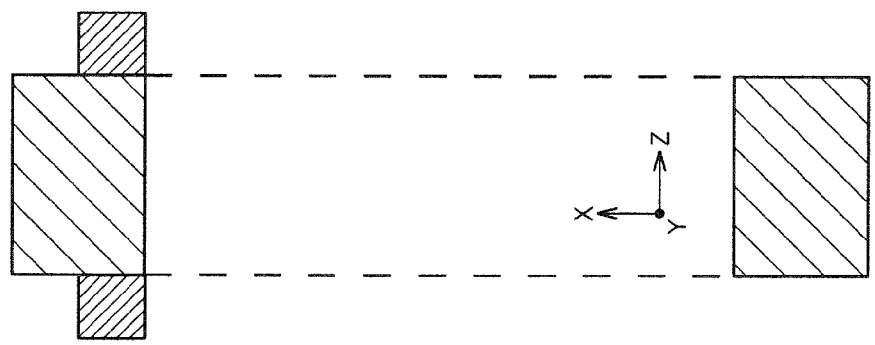
FIG. 15(b) is a vertical sectional view.
Figure 15A:
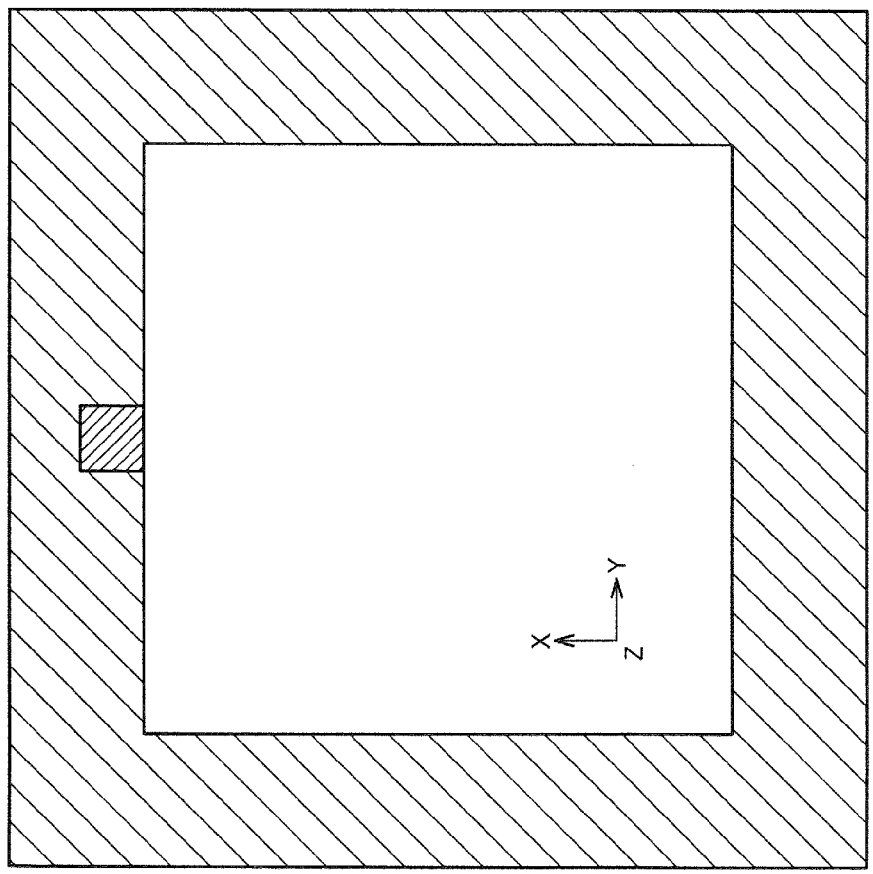
FIG. 15(a) is a front view.
Figure 16:
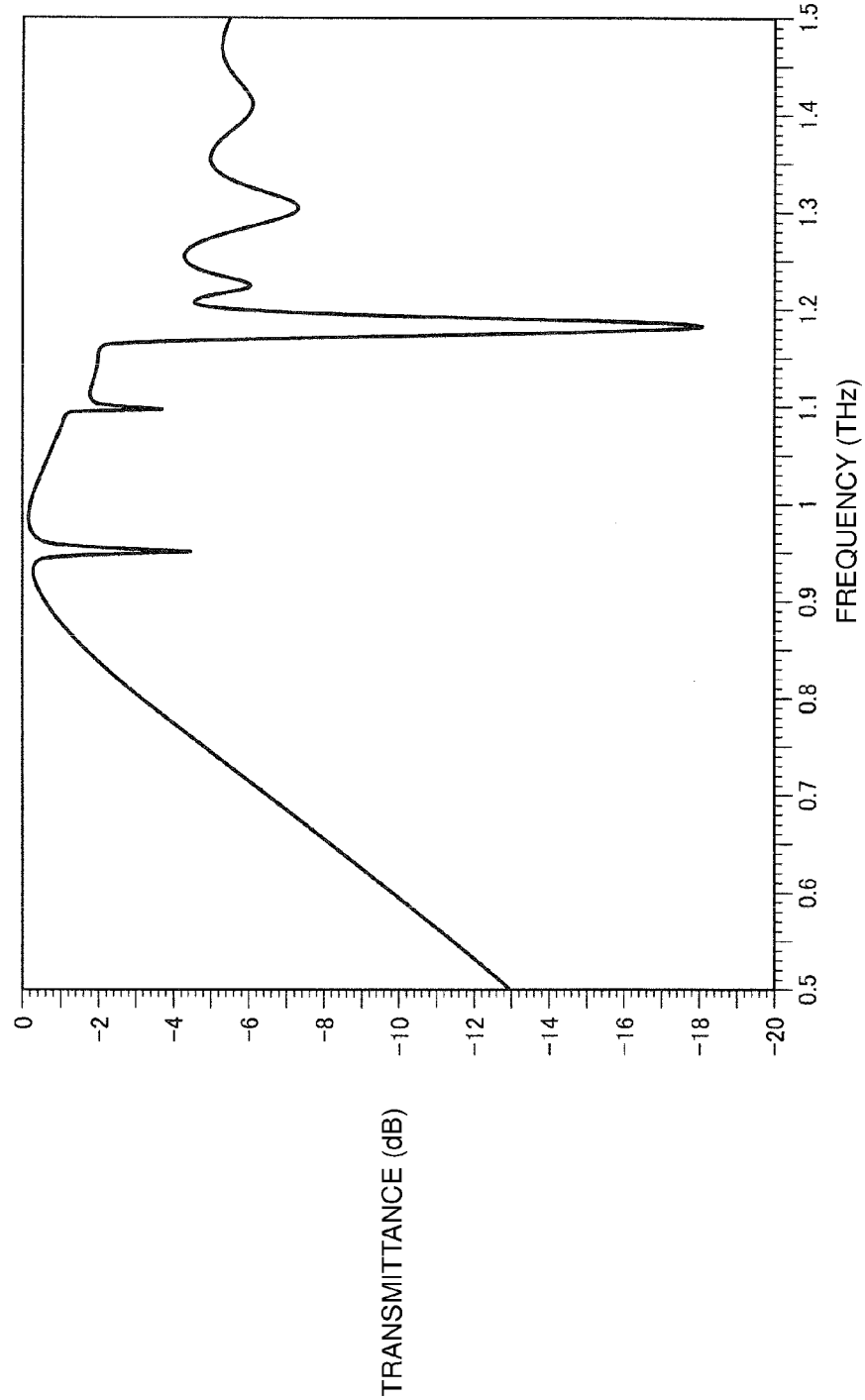
FIG. 16 is a graph depicting a frequency characteristic of transmittance obtained with the periodic structure made of the unit structure illustrated in FIG. 15.

Simulation calculation was likewise executed on a flat-plate periodic structure according to the present invention, the flat-plate periodic structure being made of a unit structure (having small projections on both sides) as illustrated in FIG. 15. FIG. 16 depicts a frequency characteristic of transmittance obtained with that simulation calculation.

Figure 17:
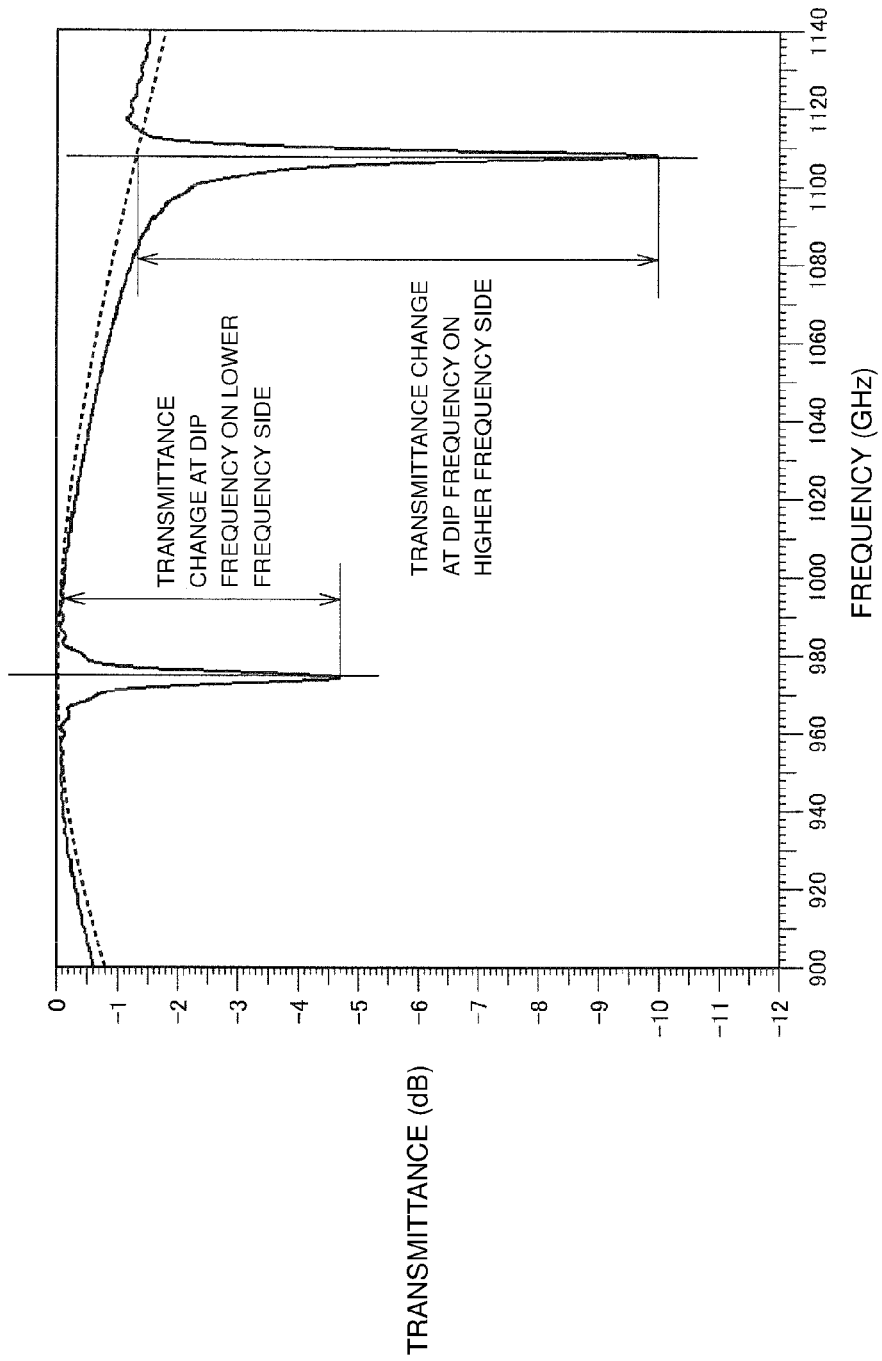
FIG. 17 is a chart to explain features in a frequency characteristic of transmittance in the present invention.

As depicted in FIG. 17, when the unit structure of the flat-plate periodic structure used in the present invention is structured such that the dip waveform appearing in the frequency characteristic of the forward-scattered electromagnetic wave or the peak waveform appearing in the frequency characteristic of the backward-scattered electromagnetic wave is produced with the TE111 mode-like resonance in the flat-plate periodic structure, a sharper dip waveform or peak waveform having a narrower band width can be obtained in comparison with the case where the electromagnetic wave is applied to the related-art flat-plate periodic structure from an oblique direction.

Figure 18:
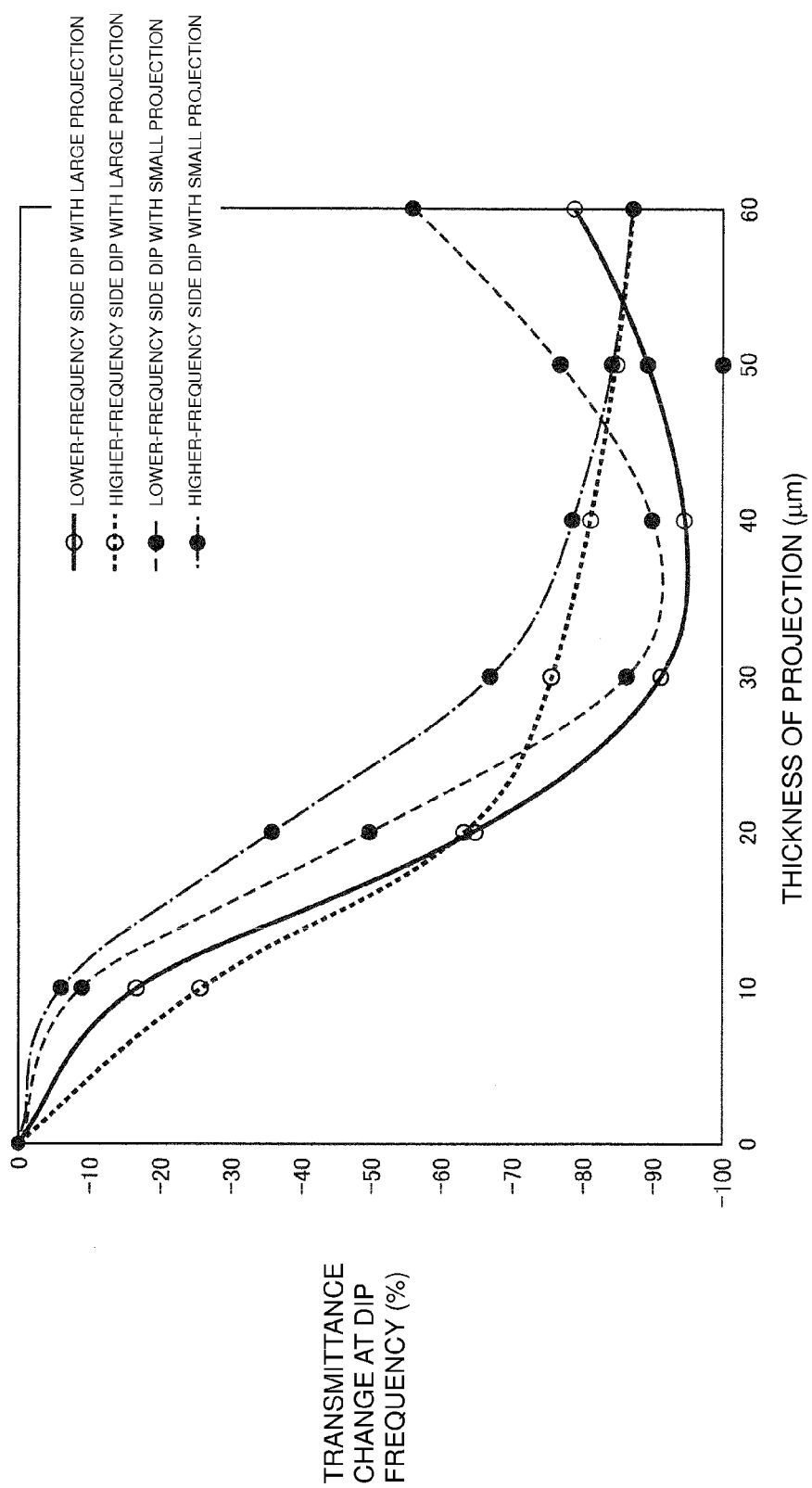
FIG. 18 is a graph depicting transmittance changes at dip frequencies in the periodic structures made of the unit structures illustrated in FIG. 3 (small projection) and FIG. 13 (large projection), respectively, when a thickness of each projection is changed.

FIG. 18 depicts transmittance changes at dip frequencies in the periodic structures made of the unit structures illustrated in FIG. 3 (small projection) and FIG. 13 (large projection), respectively, when a thickness of each projection is changed. As seen from FIG. 18, the transmittance change in the dip waveform is increased when the thickness of the large projection or the small projection is within a certain range. Assuming that the transmittance when the thickness of the projection is 0 µm (i.e., when the projection is not present) is 100%, a reduction amount of the transmittance is depicted as a minus value with respect to 100%.

Example 2

Figure 20B:
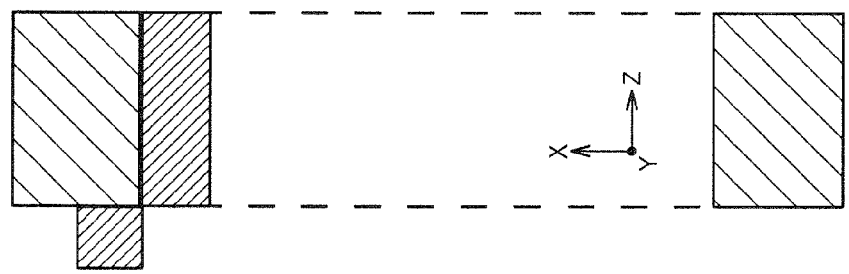
FIG. 20(b) is a vertical sectional view.
Figure 20A:
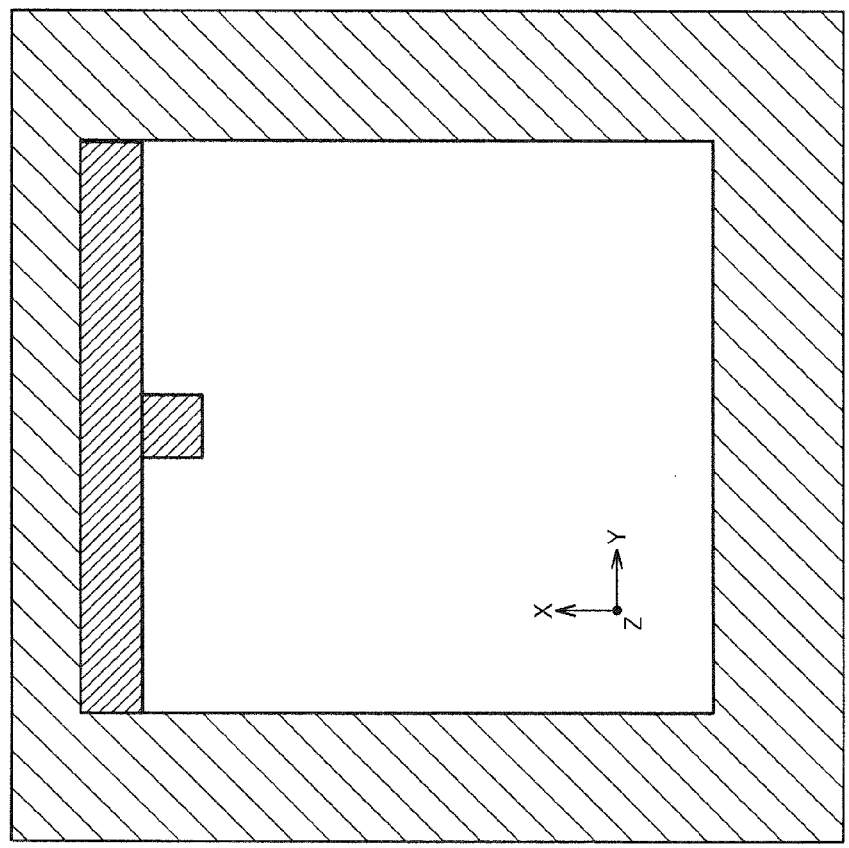
FIG. 20(a) is a front view.
Figure 21:
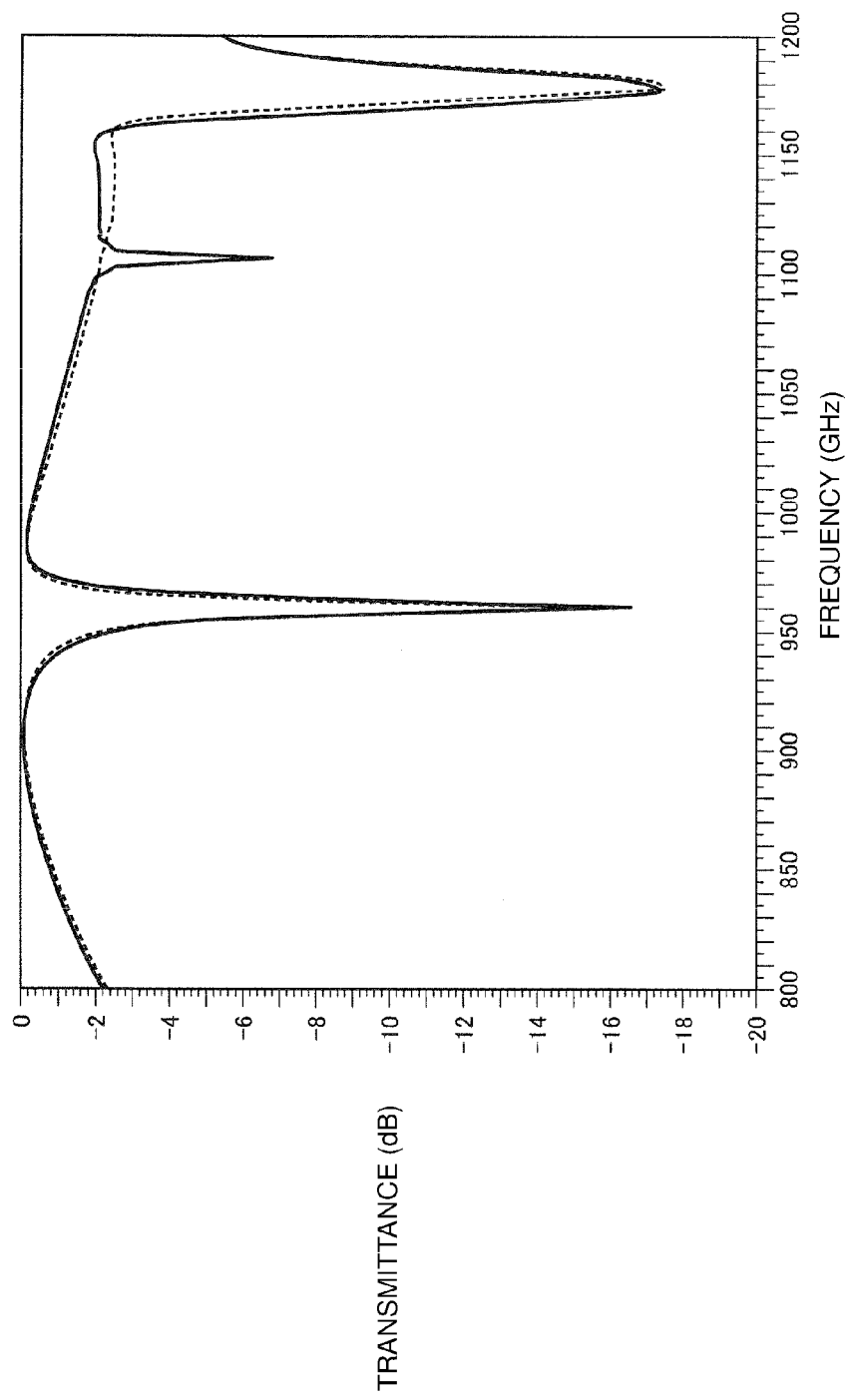
FIG. 21 is a graph depicting a frequency characteristic (dotted line) of transmittance obtained with the related-art periodic structure made of the unit structure illustrated in FIG. 19, and a frequency characteristic (solid line) of transmittance obtained with the periodic structure made of the unit structure illustrated in FIG. 20.

Simulation calculation was executed in a similar manner to that described above in EXAMPLE 1 on a prior art flat-plate periodic structure illustrated in FIG. 19 and on a flat-plate periodic structure according to the present invention, the latter periodic structure being made of a unit structure (having a large projection in addition to the structure illustrated in FIG. 19) as illustrated in FIG. 20. FIG. 21 depicts a frequency characteristic (dotted line) of transmittance obtained with the periodic structure made of the unit structure illustrated in FIG. 19, and a frequency characteristic (solid line) of transmittance obtained with the periodic structure made of the unit structure illustrated in FIG. 20. As seen from the results depicted in FIG. 21, the dip waveform produced with the TE111 mode-like resonance appears only when a sectional shape of the unit structure, taken along the polarization plane (XZ-plane) of the electromagnetic wave, is not mirror-symmetric with respect to the imaginary plane orthogonal to the polarizing direction of the electromagnetic wave because of having the projection in the Z-direction as illustrated in FIG. 20.

Likewise, simulation calculation was executed on the related-art flat-plate periodic structure illustrated in FIG. 19 and on a flat-plate periodic structure according to the present invention, the latter periodic structure being made of a unit structure (having a small projection in addition to the structure illustrated in FIG. 19) as illustrated in FIG. 22. FIG. 23 depicts a frequency characteristic (dotted line) of transmittance obtained with the periodic structure made of the unit structure illustrated in FIG. 19, and a frequency characteristic (solid line) of transmittance obtained with the periodic structure made of the unit structure illustrated in FIG. 22. As seen from the results depicted in FIG. 23, the dip waveform produced with the TE111 mode-like resonance appears only when a sectional shape of the unit structure, taken along the polarization plane (XZ-plane) of the electromagnetic wave, is not mirror-symmetric with respect to the imaginary plane orthogonal to the polarizing direction of the electromagnetic wave because of having the projection in the Z-direction as illustrated in FIG. 22.

Example 3

Figure 24B:
FIG. 24(b) is a vertical sectional view.
Figure 24A:
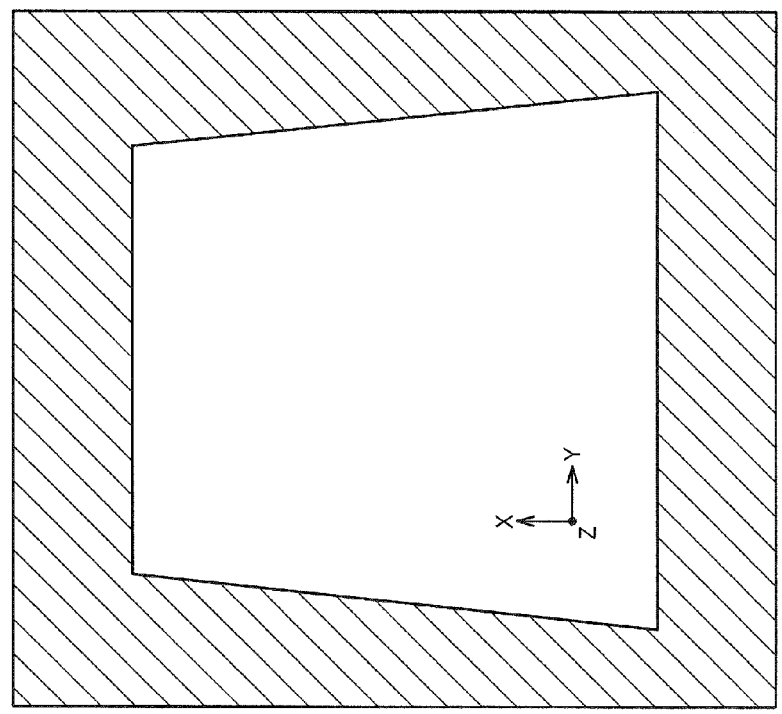
FIG. 24(a) is a front view.
Figure 25B:
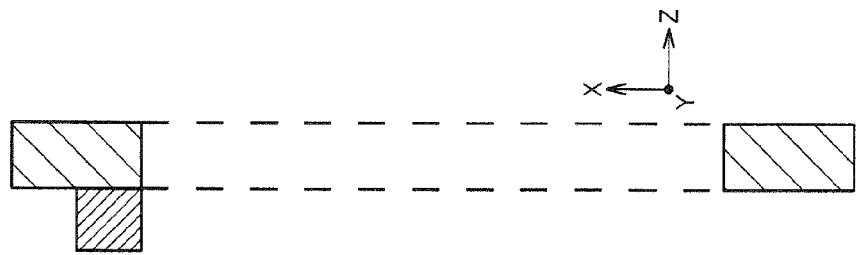
FIG. 25(b) is a vertical sectional view.
Figure 25A:
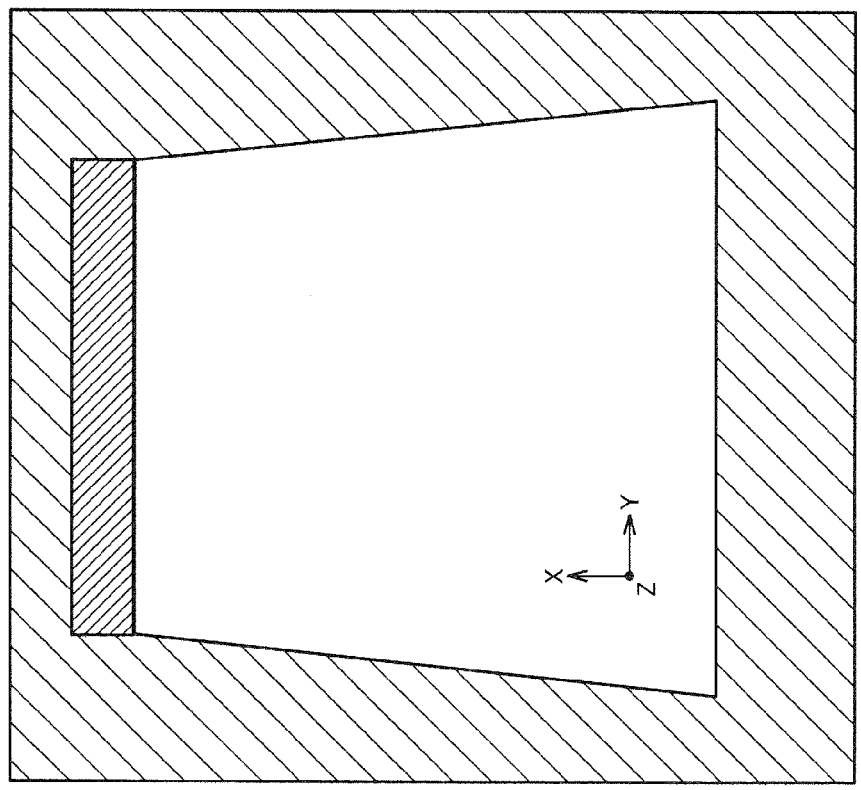
FIG. 25(a) is a front view.
Figure 26:
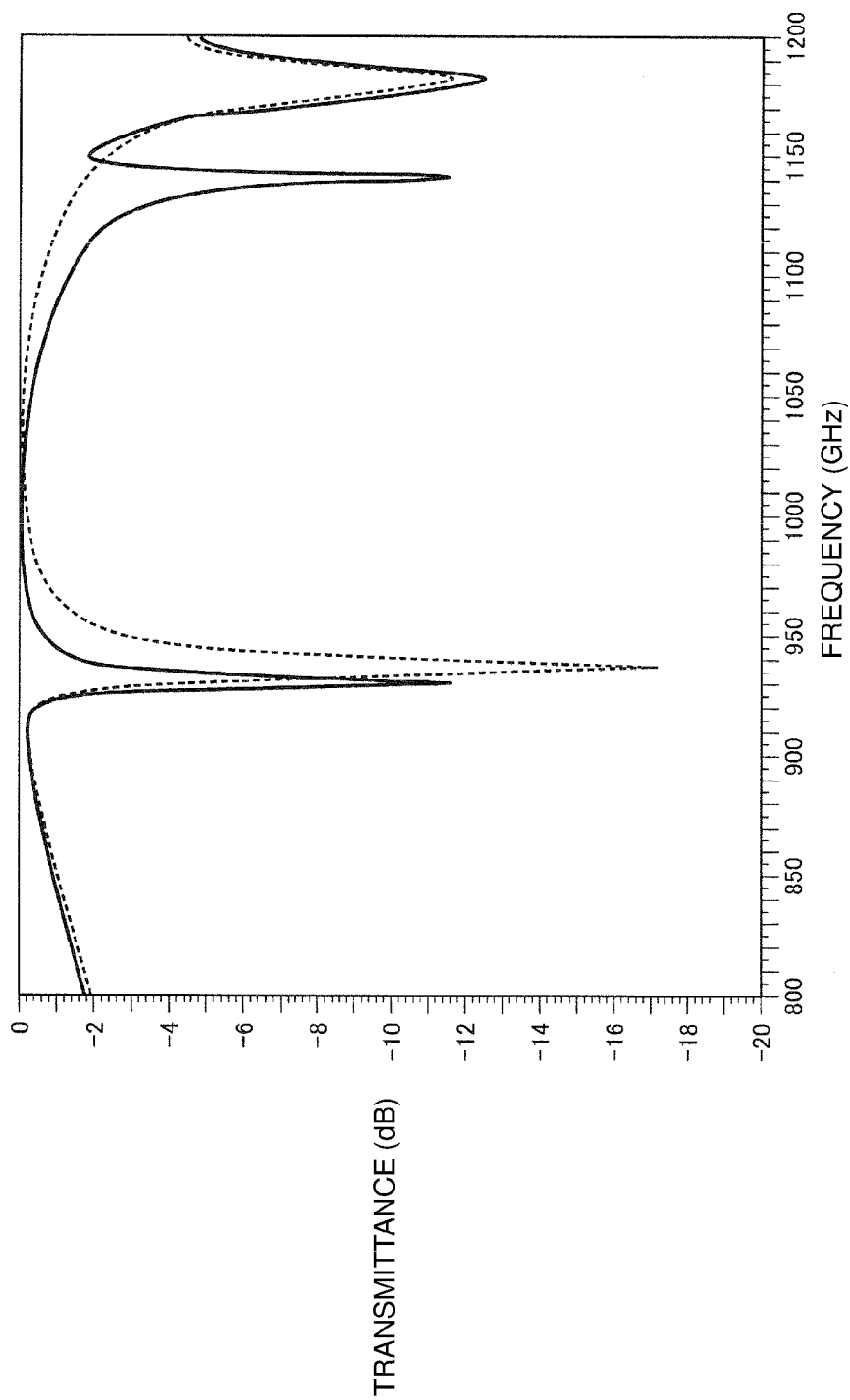
FIG. 26 is a graph depicting a frequency characteristic (dotted line) of transmittance obtained with the periodic structure made of the unit structure illustrated in FIG. 24, and a frequency characteristic (solid line) of transmittance obtained with the periodic structure made of the unit structure illustrated in FIG. 25.

Simulation calculation was executed in a similar manner to that described above in EXAMPLE 1 on a related-art flat-plate periodic structure illustrated in FIG. 24 and on a flat-plate periodic structure according to the present invention, the latter periodic structure being made of a unit structure (having a large projection in addition to the structure illustrated in FIG. 24) as illustrated in FIG. 25. FIG. 26 depicts a frequency characteristic (dotted line) of transmittance obtained with the periodic structure made of the unit structure illustrated in FIG. 24, and a frequency characteristic (solid line) of transmittance obtained with the periodic structure made of the unit structure illustrated in FIG. 25. As seen from the results depicted in FIG. 26, the dip waveform produced with the TE111 mode-like resonance appears only when a sectional shape of the unit structure, taken along the polarization plane (XZ-plane) of the electromagnetic wave, is not mirror-symmetric with respect to the imaginary plane orthogonal to the polarizing direction of the electromagnetic wave because of having the projection in the Z-direction as illustrated in FIG. 25.

Example 4

The flat-plate periodic structure made of the unit structure, illustrated in FIG. 13, was actually fabricated, and a frequency characteristic obtained when applying the electromagnetic wave to the flat-plate periodic structure was evaluated. Fabrication procedures of the flat-plate periodic structure are described below.

A conductive plate (made of Cu) having a smooth surface was prepared, and a photosensitive resin layer coated on one surface of the conductive plate was subjected to patterning by photolithography, whereby a photomask corresponding to the shape illustrated in FIG. 11 was formed. By placing the thus-obtained conductive plate in a Ni electroplating bath and supplying a current to the bath, a Ni plating film having the shape illustrated in FIG. 11 was formed in portions where the photomask was not present and the conductive plate was exposed. By removing the above-mentioned photomask and then forming another photomask in shape corresponding to the shape of each projection 101 illustrated in FIG. 13, a Ni plating film in the shape of the projection 101 was formed. The flat-plate periodic structure made of the unit structure, illustrated in FIG. 13, was obtained by removing a cured resin component, which remained on the conductive plate, with a solvent, and by peeling off a Ni plating structure from the conductive plate.

The Ni flat-plate periodic structure thus obtained was subjected to electroless Au plating, whereby the periodic structure coated with Au was obtained.

By employing the flat-plate periodic structure fabricated as described above, a frequency characteristic of the forward-scattered electromagnetic wave (i.e., the electromagnetic wave having transmitted through the periodic structure) when the electromagnetic wave was applied to the periodic structure from a direction perpendicular to the principal surface thereof was actually measured with the apparatus configuration, illustrated in FIG. 1, under the same conditions as the simulation conditions described above in EXAMPLE 1.

Figure 27:
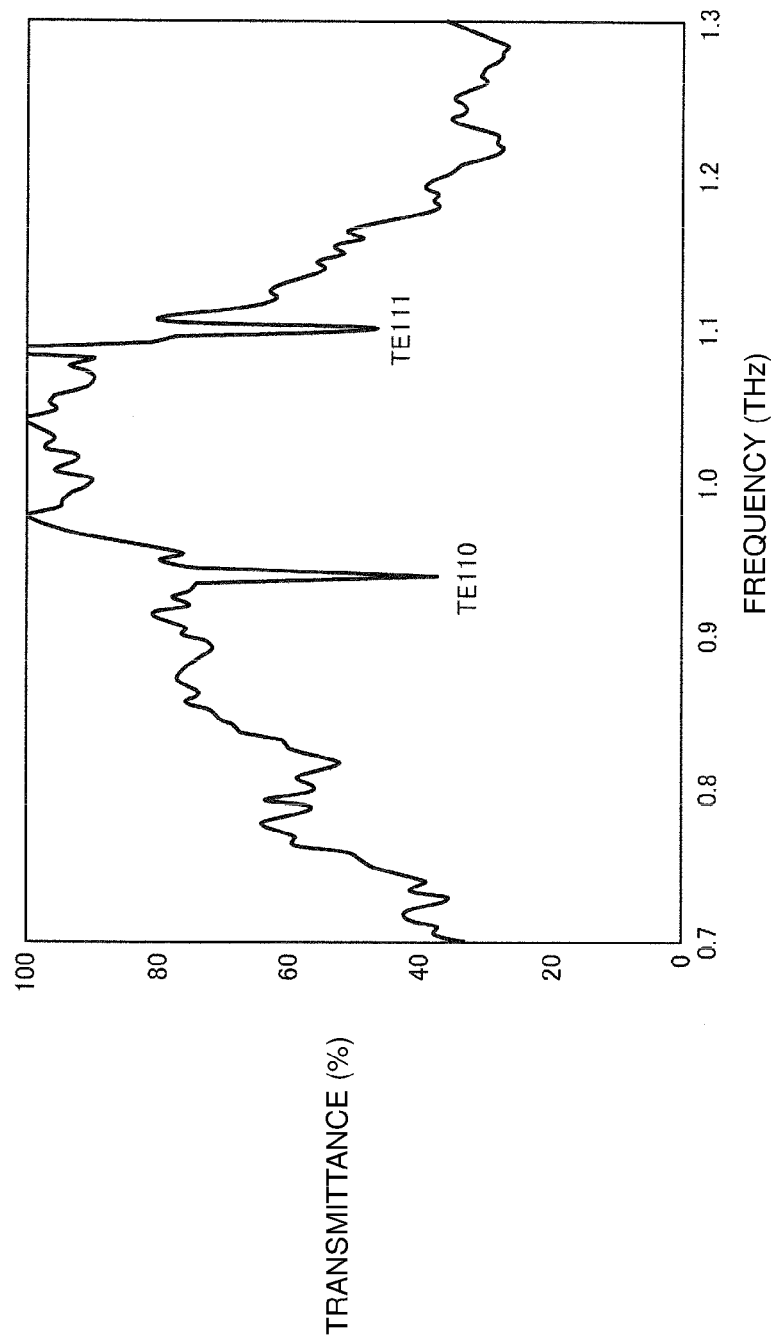
FIG. 27 is a graph depicting a frequency characteristic (actual measurement value) of transmittance obtained with the periodic structure made of the unit structure illustrated in FIG. 13.

FIG. 27 depicts a frequency characteristic actually measured on the periodic structure, illustrated in FIG. 13, as described above. From the result depicted in FIG. 27, it is understood that, as in the result of the simulation calculation depicted in FIG. 14, the dip waveform derived from the TE111 mode-like resonance is produced by applying the electromagnetic wave to the flat-plate periodic structure made of the unit structure, illustrated in FIG. 13, from the direction perpendicular to the principal surface (reference plane) of the flat-plate periodic structure.

Example 5

Figure 28:
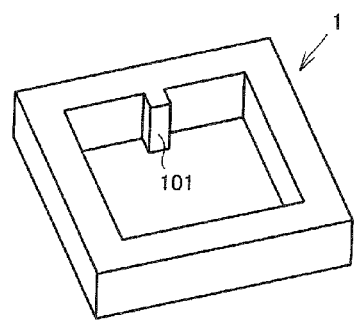
FIG. 28 is a perspective view of a unit structure constituting a flat-plate periodic structure used in EXAMPLE 5.

EXAMPLE 5 represents the case where a two dimensional shape of the aperture of the unit structure (i.e., a sectional shape taken along the reference plane defined as a surface in which the unit structures are arrayed) is not mirror-symmetric with respect to the imaginary plane orthogonal to the polarizing direction of the electromagnetic wave. FIG. 28 is a perspective view of a unit structure constituting a flat-plate periodic structure used in EXAMPLE 5. An aperture of the unit structure, illustrated in FIG. 28, has such a shape (partly recessed shape) that a projection 101 is disposed near a central portion of one of side surfaces of the aperture. The flat-plate periodic structure made of the unit structure, illustrated in FIG. 28, was actually fabricated, and a frequency characteristic was actually measured when the electromagnetic wave was applied to the periodic structure. Fabrication procedures of the periodic structure are described below.

First, a conductive plate (made of Cu) having a smooth surface with a 300-mm square was prepared, and a photosensitive resin layer was coated in a thickness of 100 μm on one surface of the conductive plate and then dried. Subsequently, a photomask corresponding to portions other than the apertures of the periodic structure was formed, and portions of the photosensitive resin layer corresponding to the apertures were UV-cured. A non-cured resin component was removed by rinsing such that the conductive plate was exposed. By placing the thus-obtained conductive plate in a Ni electrolytic plating bath and supplying a current to the bath, a Ni plating film having a thickness of 20 μm was formed only in portions where the cured photosensitive resin layer was not present and the conductive plate was exposed. After the plating, by removing a cured resin component, which remained on the conductive plate, with a solvent, and by peeling off a Ni plating structure from the conductive plate, the flat-plate periodic structure made of Ni and having a thickness of 20 μm was obtained in which the unit structures, each illustrated in FIG. 28, were arrayed in a square lattice pattern (with a lattice spacing of 260 μm). Each of the unit structures had dimensions of 260×260 μm when viewed in a normal direction to the periodic structure, and had an aperture of 180×180 μm. A projection 101 (having a cubic shape of 20×20×20 μm) was disposed in a central portion of one side surface of the aperture. Then, the Ni flat-plate periodic structure thus obtained was subjected to electroless Au plating, whereby the periodic structure (metal mesh) coated with Au was obtained.

A transmittance spectrum of the electromagnetic wave having transmitted through the periodic structure was measured in a similar manner to that described in EXAMPLE 4 by the THz-TDS when the electromagnetic wave was applied to the metal mesh from a direction perpendicular to the principal surface thereof.

The measurement was performed when a parallel beam was applied as the electromagnetic wave, and when a converted beam was applied as the electromagnetic wave. In the case applying the parallel beam (plane wave), assuming that a surface perpendicular to an optical axis (i.e., to the propagating direction of the electromagnetic wave) is specified in the THz-TDS used in the experiment, phases of the electromagnetic wave emitted from the light source in the above-mentioned surface are the same. Accordingly, when the metal mesh is set perpendicularly to the optical axis, the phases of the electromagnetic wave in the principal surface of the periodic structure are the same and respective phases of the electromagnetic wave applied to the individual apertures are the same on condition that the electromagnetic wave applied to the principal surface of the metal mesh is a plane wave.

Figure 29:
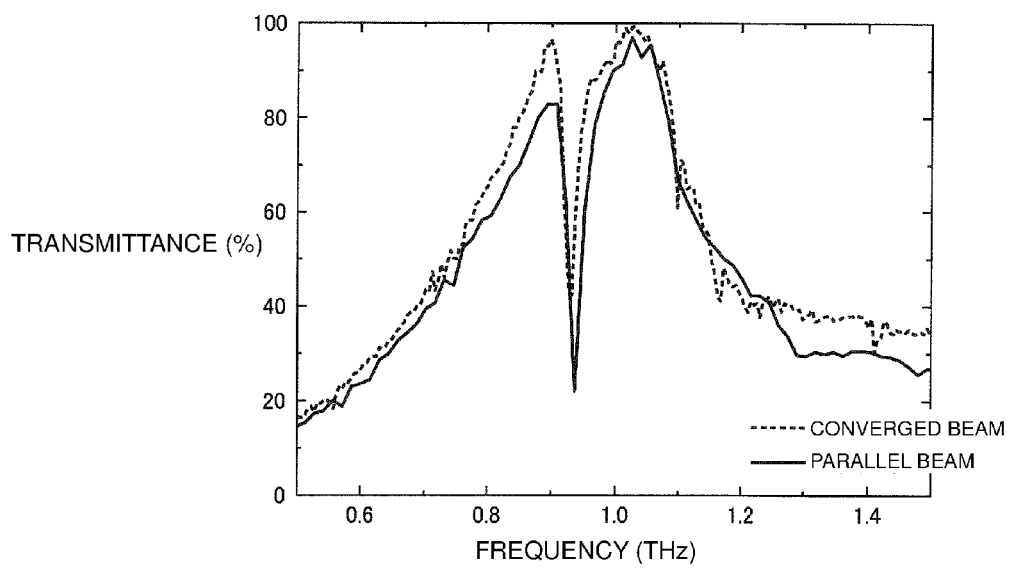
FIG. 29 is a graph depicting a frequency characteristic (actual measurement value) of transmittance obtained with the periodic structure made of the unit structure illustrated in FIG. 28.

FIG. 29 depicts the measurement results of the frequency characteristic. In FIG. 29, a solid line represents the frequency characteristic when the parallel beam is applied, and a dotted line represents the frequency characteristic when the converged beam is applied. As seen from FIG. 29, the dip waveform appearing in the frequency characteristic (solid line) when the parallel beam is applied has a narrower band width and is sharper than the dip waveform appearing in the frequency characteristic (dotted line) when the converged beam is applied. From those results, it is understood that the dip waveform in the transmittance spectrum is sharpened and the characteristics of the specimen can be measured with higher sensitivity by applying the parallel beam in comparison with the case applying the converged beam.

Example 6

Figure 30:
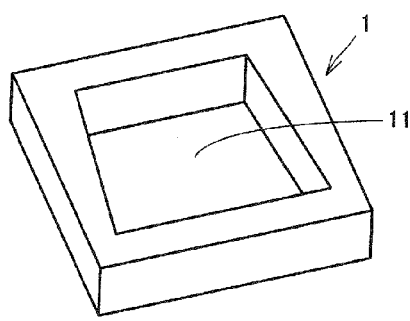
FIG. 30 is a perspective view of a unit structure constituting a flat-plate periodic structure used in EXAMPLE 6.

EXAMPLE 6 is another example representing the case where a two dimensional shape of the aperture of the unit structure (i.e., a sectional shape taken along the reference plane defined as a surface in which the unit structures are arrayed) is not mirror-symmetric with respect to the imaginary plane orthogonal to the polarizing direction of the electromagnetic wave. FIG. 30 is a perspective view of a unit structure constituting a flat-plate periodic structure used in EXAMPLE 6. An aperture of the unit structure, illustrated in FIG. 30, has a trapezoidal shape (when viewed from a direction perpendicular to a principal surface of the periodic structure). The periodic structure of EXAMPLE 6 was fabricated in a similar manner to that described above in EXAMPLE 5 except that the aperture of the unit structure had a trapezoidal shape (with an upper bottom of 160 µm, a lower bottom of 200 µm, and a height of 180 µm). Subsequently, a frequency characteristic was measured in a similar manner to that described above in EXAMPLE 5.

Figure 31:
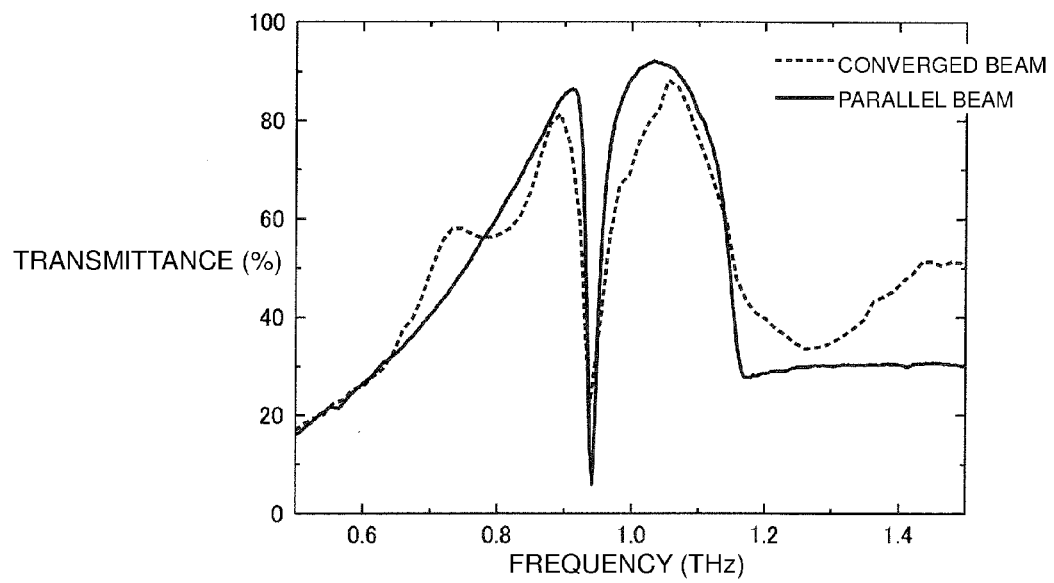
FIG. 31 is a graph depicting a frequency characteristic (actual measurement value) of transmittance obtained with the periodic structure made of the unit structure illustrated in FIG. 30.

FIG. 31 depicts the measurement results of the frequency characteristic. In FIG. 31, a solid line represents the frequency characteristic when the parallel beam is applied, and a dotted line represents the frequency characteristic when the converged beam is applied. As seen from FIG. 31, the dip waveform appearing in the frequency characteristic (solid line) when the parallel beam is applied has a narrower band width and is sharper than the dip waveform appearing in the frequency characteristic (dotted line) when the converged beam is applied. From those results, it is understood that the dip waveform in the transmittance spectrum is sharpened and the characteristics of the specimen can be measured with higher sensitivity by applying the parallel beam in comparison with the case applying the converged beam.

Example 7

Figure 32:
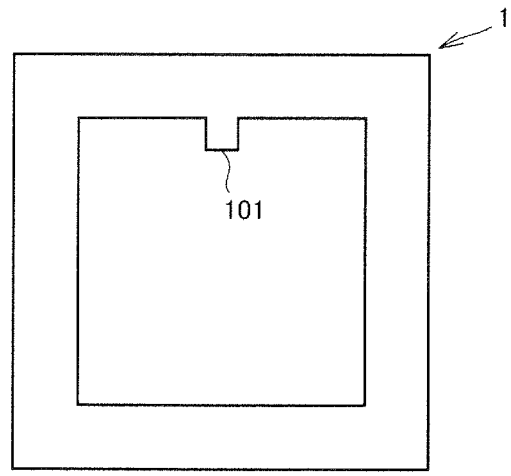
FIG. 32 is a front view of the unit structure illustrated in FIG. 28.
Figure 33:
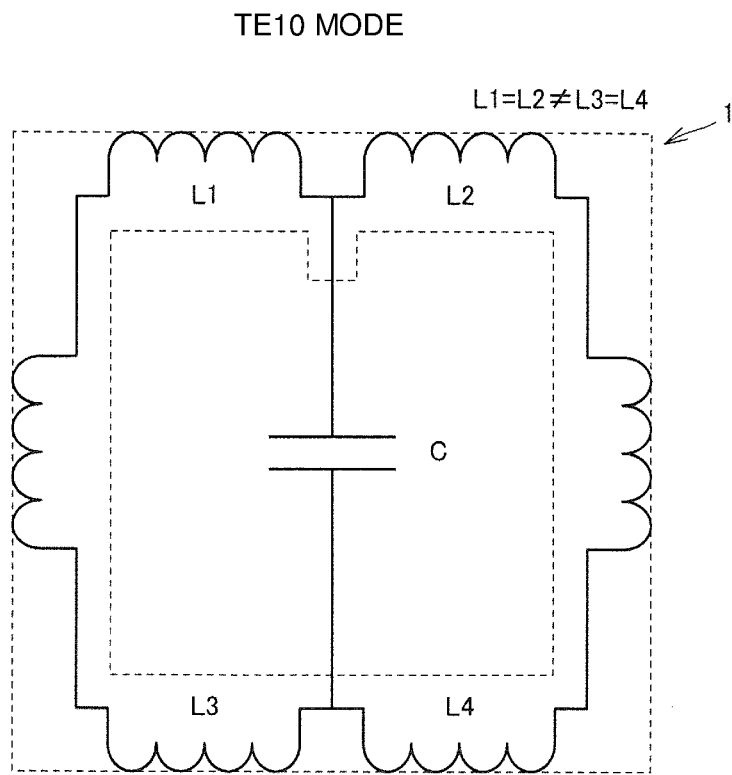
FIG. 33 is a circuit diagram representing, as an equivalent circuit, a state of the unit structure illustrated in FIG. 32 when TE110 mode-like resonance is produced.
Figure 34:
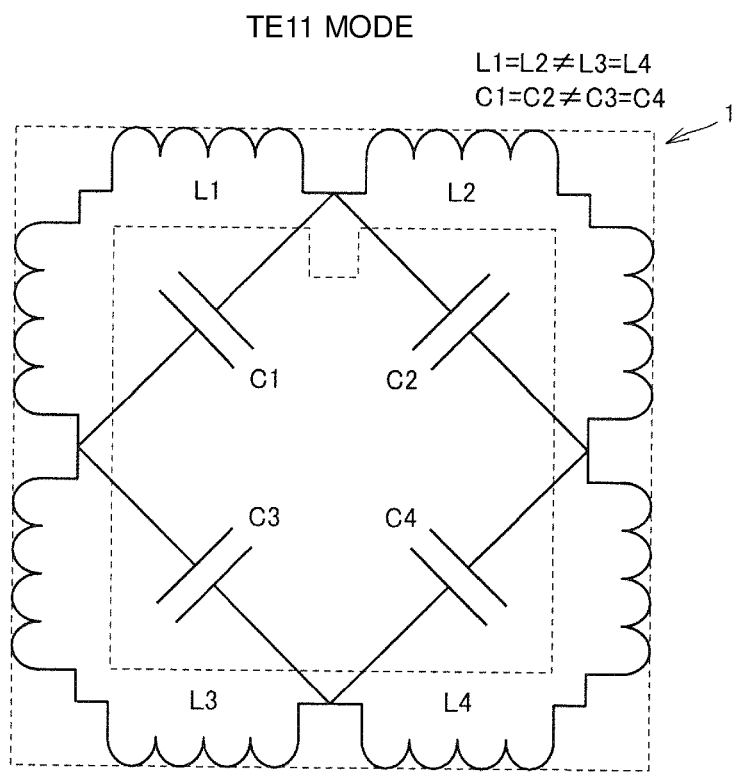
FIG. 34 is a circuit diagram representing, as an equivalent circuit, a state of the unit structure illustrated in FIG. 32 when TE111 mode-like resonance is produced.

EXAMPLE 7 represents the case executing simulation calculation on the periodic structure made of the unit structure illustrated in FIG. 28, which is the same as that in EXAMPLE 5, by employing an equivalent circuit. FIG. 32 is a front view of the unit structure illustrated in FIG. 28. FIG. 33 is a circuit diagram representing, as an equivalent circuit, a state of the unit structure illustrated in FIG. 32 when TE10 mode-like (pseudo TE10 mode) resonance is produced. FIG. 34 is a circuit diagram representing, as an equivalent circuit, a state of the unit structure illustrated in FIG. 32 when TE11 mode-like (pseudo TE11 mode) resonance is produced.

Figure 35:
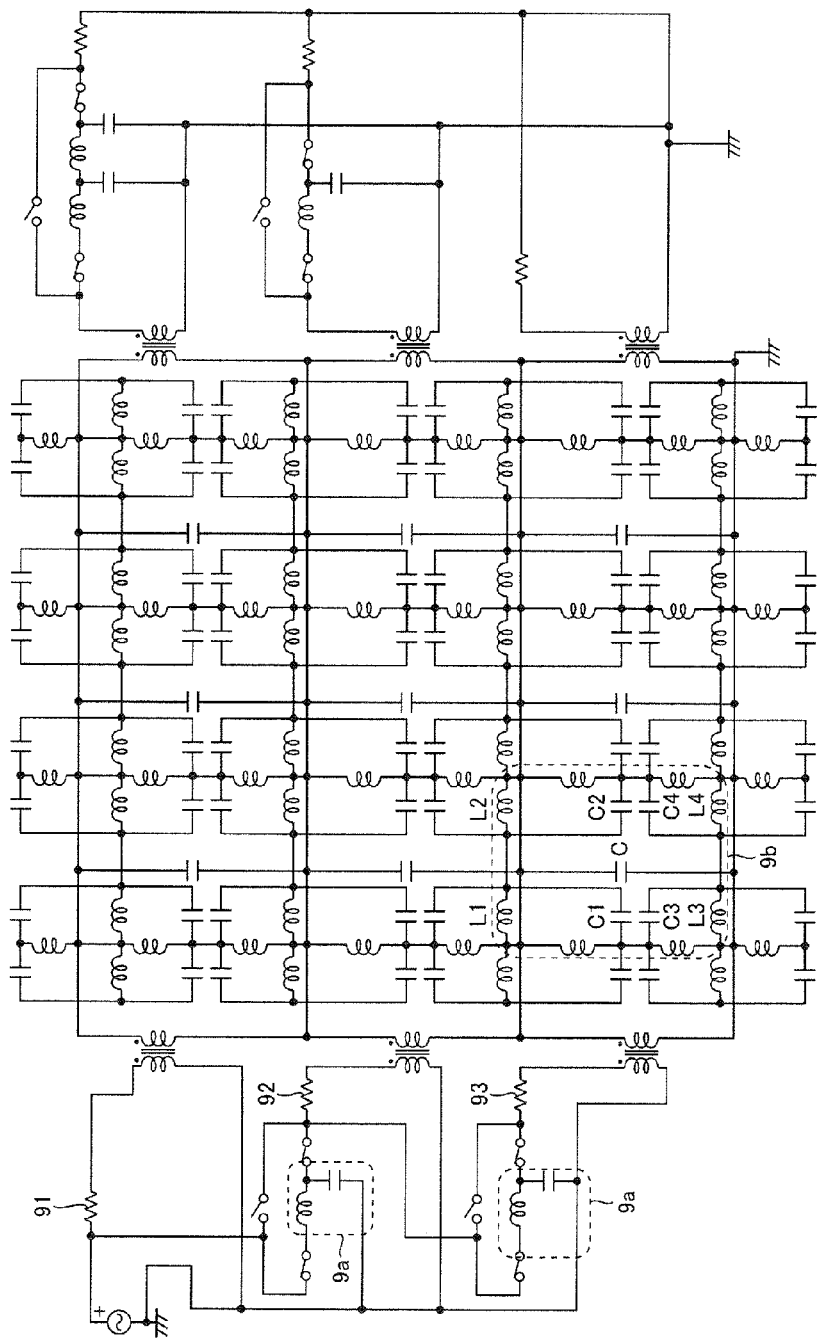
FIG. 35 is a circuit diagram representing, as an equivalent circuit, a state of a periodic structure made of the unit structure illustrated in FIG. 32 when the TE111 mode-like resonance is produced.

FIG. 35 is a circuit diagram representing, as an equivalent circuit, a periodic structure (metal mesh) made of nine unit structures, illustrated in FIGS. 28 and 32, in a square lattice pattern (three in a vertical direction and three in a horizontal direction). In FIG. 35, a portion 9b corresponding to one unit structure is constituted by a circuit in combination of the equivalent circuit illustrated in FIG. 33 (when the pseudo TE10 mode resonance is produced) and the equivalent circuit illustrated in FIG. 34 (when the pseudo TE11 mode resonance is produced). The equivalent circuit of FIG. 35 includes two phase delay circuits 9a such that a signal phase can be varied by changing over switches. The equivalent circuit in the pseudo TE10 mode (when the electromagnetic wave having different phases is input) and the equivalent circuit in the pseudo TE11 mode (when the electromagnetic wave having the same phase is input) can be switched over by varying the signal phase.

Figure 36:
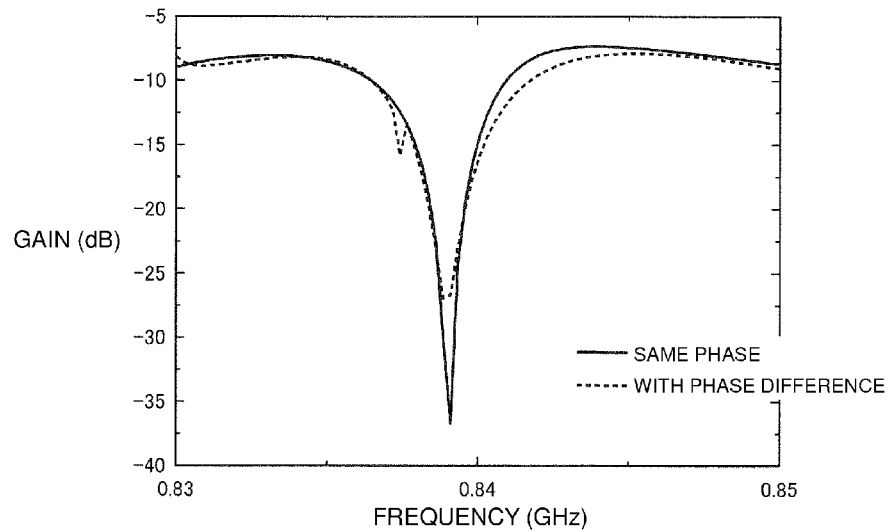
FIG. 36 is a graph depicting an output waveform of the equivalent circuit (i.e., frequency characteristics of transmittance obtained with the periodic structure), which is obtained with simulation calculation using the equivalent circuit represented as the circuit diagram of FIG. 35, the graph depicting results with respect to the phase of an incident electromagnetic wave.

The output of the equivalent circuit illustrated in FIG. 35 was calculated using a circuit simulator (circuitviewer 4.0) made by Micronet Co. Because the software did not run in a terahertz band, circuit parameters were set such that the dip waveform appeared near 0.8 GHz. More specifically, values of coils (L1 and L3) and values of capacitor capacitances (C, C1, and C3) in the equivalent circuits of FIGS. 33 and 34 were set respectively to L1=16.5 nH, L3=18 nH, C=0.93 pF, C1=0.93 pF, and C3=0.8 pF. Frequency resolution was set to 240 kHz. FIG. 36 depicts calculated output waveforms (corresponding to frequency characteristics of transmittance) of the equivalent circuit.

In the graph of FIG. 36, a solid line represents the calculation result of the output waveform of the equivalent circuit (i.e., the equivalent circuit in the pseudo TE11 mode) when the electromagnetic wave having the same phase is input to the entire equivalent circuit that corresponds to the periodic structure including the nine unit structures. A dotted line represents the calculation result of the output waveform of the equivalent circuit (i.e., the equivalent circuit in the pseudo TE10 mode) when signals are input to upper, middle and lower stages of the equivalent circuit, illustrated in FIG. 35, with a phase difference of 0.55 rad between the adjacent stages.

From the results depicted in FIG. 36, it is understood that the dip waveform in the transmittance spectrum is sharpened and the characteristics of the specimen can be measured with higher sensitivity when the signals input to the adjacent apertures have the same phase (i.e., when the phases of the electromagnetic wave in the principal surface of the periodic structure are the same).

Example 8

Figure 37:
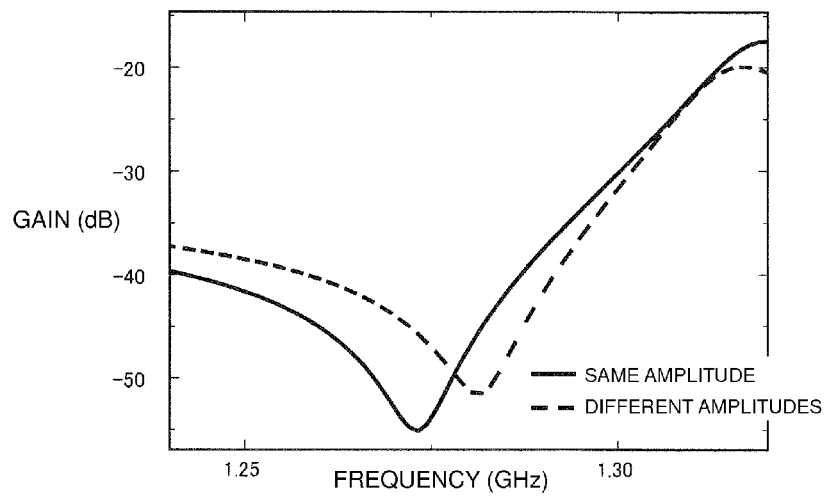
FIG. 37 is a graph depicting an output waveform of the equivalent circuit (i.e., a frequency characteristics of transmittance obtained with the periodic structure), which is obtained with simulation calculation using the equivalent circuit represented as the circuit diagram of FIG. 35, the graph depicting results with respect to the amplitude of the incident electromagnetic wave.

The equivalent circuit, illustrated in FIG. 35 and described in EXAMPLE 7, includes a resistance 91, a resistance 92, and a resistance 93, and the amplitude of each signal can be varied by changing a corresponding resistance value. In EXAMPLE 8, an output of the equivalent circuit was calculated using the circuit simulator (circuitviewer 4.0) made by Micronet Co. when the amplitude was varied. Because the software did not run in a terahertz band, the circuit parameters were set such that the dip waveform appeared near 1.27 GHz. More specifically, values of coils (L1 and L3) and values of capacitor capacitances (C, C1, and C3) in the equivalent circuits of FIGS. 33, 34 were set respectively to L1=16.5 nH, L3=18.0 nH, C=0.93 pF, C1=0.93 pF, and C3=1.2 pF. Frequency resolution was set to 120 kHz. FIG. 37 depicts calculated output waveforms of the equivalent circuit.

In the graph of FIG. 37, a solid line represents the calculation result of the output waveform of the equivalent circuit when the electromagnetic wave having the same phase and the same amplitude is input to the equivalent circuit representing the nine apertures. A dotted line represents the calculation result of the output waveform of the equivalent circuit when signals having the same phase are input to the upper, middle and lower stages of the equivalent circuit, illustrated in FIG. 35, with the amplitude of the electromagnetic wave differing between the adjacent stages.

From the results depicted in FIG. 37, it is understood that the dip waveform in the transmittance spectrum is sharpened and the characteristics of the specimen can be measured with higher sensitivity when the signals input to the adjacent apertures have the same amplitude (i.e., when the amplitudes of the electromagnetic wave in the principal surface of the periodic structure are the same).

Similar advantageous effects to those obtained with the above-described EXAMPLES can also be obtained by employing a periodic structure made of a unit structure having another shape (e.g., a convex shape, a regular pentagonal shape, or a star-like shape), which satisfies the conditions required in the present invention, without being limited to the unit structure having the shape illustrated in any of the above-described EXAMPLES. Furthermore, while the above-described EXAMPLES employ the periodic structures in each of which the unit structures are periodically arrayed in a square lattice pattern (i.e., in a square lattice array) in the direction of the principal surface of the periodic structure, the similar advantageous can further be obtained with a periodic structure in which unit structures are arrayed in a triangular lattice pattern, for example, on condition that the unit structure has a shape satisfying the conditions required in the present invention.

The embodiments and EXAMPLES disclosed here are to be considered as illustrative in all respects, not as restrictive. The scope of the present invention is defined in the appended claims, not by the foregoing description, and it is intended to involve all modifications being equivalent in meaning to the appended claims and falling within the scope defined in the appended claims.

REFERENCE SIGNS LIST 1 flat-plate periodic structure, 10a principal surface, 10b side surface, 101 projection, 11 aperture, 11a side surface of aperture, 2 laser, 20 half mirror, 21 mirror, 22, 23, 24, 25 parabolic mirrors, 26 time delay stage, 3 power supply, 4 lock-in amplifier, 5 PC (personal computer), 6 amplifier, 71, 72 photoconductive elements, 8 oscillator, 9a phase delay circuit, and 91, 92, 93 resistances.

The invention claimed is:

1. A measuring method comprising:
holding a specimen on a flat-plate periodic structure;
applying a linearly-polarized electromagnetic wave to the periodic structure:
detecting the electromagnetic wave scattered forward or backward by the periodic structure and
measuring characteristics of the specimen based on a phenomenon that a dip waveform appearing in a frequency characteristic of the forward-scattered electromagnetic wave or a peak waveform appearing in a frequency characteristic of the backward-scattered electromagnetic wave is changed with the presence of the specimen,
wherein the periodic structure comprises plural unit structures having the same shape two-dimensionally and periodically interconnected in a direction of one reference plane,
the unit structures have at least one aperture penetrating therethrough in a direction perpendicular to the reference plane,
the electromagnetic wave is applied from a direction substantially perpendicular to the reference plane, and
the unit structures have a shape that is not mirror-symmetric with respect to an imaginary plane orthogonal to a polarizing direction of the electromagnetic wave.

2. The measuring method according to claim 1, wherein a sectional shape of the unit structure, taken along a polarization plane of the electromagnetic wave, is not mirror-symmetric with respect to the imaginary plane orthogonal to the polarizing direction of the electromagnetic wave.

3. The measuring method according to claim 2, wherein the dip waveform appearing in the frequency characteristic of the forward-scattered electromagnetic wave or the peak waveform appearing in the frequency characteristic of the backward-scattered electromagnetic wave is produced with TE111 mode-like resonance in the periodic structure.

4. The measuring method according to claim 2, wherein a projection is disposed on a principal surface of the unit structures on a side of the unit structures opposite to the other side where the specimen is held.

5. The measuring method according to claim 1, wherein a sectional shape of the aperture of the unit structure, taken along the reference plane, is not mirror-symmetric with respect to the imaginary plane orthogonal to the polarizing direction of the electromagnetic wave.

6. The measuring method according to claim 5, wherein the electromagnetic wave applied to the periodic structure is a plane wave.

7. The measuring method according to claim 5, wherein the electromagnetic wave is applied such that phases of the electromagnetic wave in a principal surface of the periodic structure are substantially the same within at least a range exposed to irradiation with the electromagnetic wave.

8. The measuring method according to claim 5, wherein the electromagnetic wave is applied such that amplitudes of the electromagnetic wave in a principal surface of the periodic structure are substantially the same within at least a range exposed to irradiation with the electromagnetic wave.

9. A flat-plate periodic structure for use in the measuring method according to claim 1,
comprising plural unit structures having the same shape two-dimensionally and periodically interconnected in a direction of one reference plane,
the unit structures having at least one aperture penetrating therethrough in a direction perpendicular to the reference plane,
the structures adapted to have an electromagnetic wave applied from a direction perpendicular to the reference plane, and
the unit structures having a shape that is not mirror-symmetric with respect to an imaginary plane orthogonal to a polarizing direction of the electromagnetic wave.

10. The flat-plate periodic structure according to claim 9, having a projection disposed on a principal surface of the unit structure on a side of the unit structures opposite to the side where a specimen is to be held.

11. The flat-plate periodic structure according to claim 10, wherein a sectional shape of the aperture of the unit structure, taken along the reference plane, is not mirror-symmetric with respect to the imaginary plane orthogonal to the polarizing direction of the electromagnetic wave.

12. The flat-plate periodic structure according to claim 9, wherein a sectional shape of the aperture of the unit structures, taken along the reference plane, is not mirror-symmetric with respect to the imaginary plane orthogonal to the polarizing direction of the electromagnetic wave.

* * * * *